(12) United States Patent
Cabrera et al.

(10) Patent No.: US 8,777,961 B2
(45) Date of Patent: Jul. 15, 2014

(54) SURGICAL RETRIEVAL APPARATUS

(75) Inventors: Ramiro Cabrera, Cheshire, CT (US);
Alistair Fleming, Lower Cambourne (GB); Simon Roderick Grover, Cambridge (GB); Charles Alan Seegert, Irving, TX (US)

(73) Assignee: Covidien LP, Mansfield, MA (US)

( * ) Notice: Subject to any disclaimer, the term of this patent is extended or adjusted under 35 U.S.C. 154(b) by 226 days.

(21) Appl. No.: 13/235,603

(22) Filed: Sep. 19, 2011

(65) Prior Publication Data

US 2012/0083797 A1   Apr. 5, 2012

Related U.S. Application Data

(60) Provisional application No. 61/499,923, filed on Jun. 22, 2011, provisional application No. 61/430,206, filed on Jan. 6, 2011, provisional application No. 61/389,391, filed on Oct. 4, 2010.

(51) Int. Cl.
*A61B 17/24* (2006.01)
*A61B 17/00* (2006.01)
*A61B 17/221* (2006.01)

(52) U.S. Cl.
CPC ........ *A61B 17/00234* (2013.01); *A61B 17/221* (2013.01); *A61B 2017/00287* (2013.01)
USPC ...................................................... 606/114

(58) Field of Classification Search
USPC ......... 606/110, 114, 127, 128, 141, 142, 200, 606/108; 604/317, 540; 600/562
See application file for complete search history.

(56) References Cited

U.S. PATENT DOCUMENTS

| 30,471 | A | 10/1860 | Dudley |
| 35,164 | A | 5/1862 | Logan et al. |
| 156,477 | A | 11/1874 | Bradford |
| 1,609,014 | A | 11/1926 | Dowd |
| 3,800,781 | A | 4/1974 | Zalucki |
| 4,557,255 | A | 12/1985 | Goodman |
| 4,611,594 | A | 9/1986 | Grayhack et al. |
| 4,744,363 | A | 5/1988 | Hasson |
| 4,790,812 | A | 12/1988 | Hawkins, Jr. et al. |
| 4,927,427 | A | 5/1990 | Kriauciunas et al. |
| 4,997,435 | A | 3/1991 | Demeter |
| 5,037,379 | A | 8/1991 | Clayman et al. |

(Continued)

FOREIGN PATENT DOCUMENTS

| DE | 8435489 | 12/1984 |
| DE | 3542667 | 6/1986 |

(Continued)

OTHER PUBLICATIONS

European Search Report from corresponding EP 11 25 0836 dated Sep. 12, 2013.

*Primary Examiner* — Ryan Severson
*Assistant Examiner* — Anh Dang

(57) ABSTRACT

A surgical retrieval apparatus includes a housing having an elongated sleeve extending therefrom that, together, cooperate to define a lumen extending therethrough. A shaft having an end effector assembly disposed at a distal end thereof is selectively translatable between a first position, wherein the end effector assembly is disposed within the sleeve, and a second position, wherein the end effector assembly extends distally from the sleeve. A specimen retrieval bag is releasably coupled to the end effector assembly and is deployable to an extended position upon movement of the end effector assembly from the first to the second position.

15 Claims, 20 Drawing Sheets

(56) References Cited

U.S. PATENT DOCUMENTS

| | | |
|---|---|---|
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,735,289 A | 4/1998 | Pfeffer et al. |
| 5,755,724 A | 5/1998 | Yoon |
| 5,759,187 A | 6/1998 | Nakao et al. |
| 5,769,794 A | 6/1998 | Conlan et al. |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,836,953 A | 11/1998 | Yoon |
| 5,853,374 A | 12/1998 | Hart et al. |
| 5,895,392 A | 4/1999 | Riek et al. |
| 5,906,621 A | 5/1999 | Secrest et al. |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternström |
| 6,162,235 A | 12/2000 | Vaitekunas |
| 6,165,121 A | 12/2000 | Alferness |
| 6,168,603 B1 | 1/2001 | Leslie et al. |
| 6,228,095 B1 | 5/2001 | Dennis |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,383,195 B1 | 5/2002 | Richard |
| 6,383,196 B1 | 5/2002 | Leslie et al. |
| 6,383,197 B1 | 5/2002 | Conlon et al. |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,994,696 B2 | 2/2006 | Suga |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 2004/0097960 A1 | 5/2004 | Terachi et al. |
| 2004/0138587 A1 | 7/2004 | Lyons |
| 2005/0267492 A1 | 12/2005 | Poncet et al. |
| 2006/0052799 A1 | 3/2006 | Middleman et al. |
| 2006/0058776 A1 | 3/2006 | Bilsbury |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2008/0188766 A1 | 8/2008 | Gertner |
| 2008/0221588 A1 | 9/2008 | Hollis et al. |
| 2008/0234696 A1 | 9/2008 | Taylor et al. |
| 2008/0300621 A1 | 12/2008 | Hopkins et al. |
| 2008/0312496 A1 | 12/2008 | Zwolinski |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2011/0190781 A1 | 8/2011 | Collier et al. |
| 2011/0299799 A1 | 12/2011 | Towe |

FOREIGN PATENT DOCUMENTS

| | | |
|---|---|---|
| DE | 42 04 210 | 8/1992 |
| DE | 196 24 826 | 1/1998 |
| EP | 2184014 | 5/2010 |
| FR | 1272412 | 9/1961 |
| WO | WO 93/15675 | 8/1993 |
| WO | WO 95/09666 | 4/1995 |
| WO | WO 2004/002334 A1 | 1/2004 |
| WO | 2004/112571 A2 | 12/2004 |
| WO | 2005/112783 A1 | 12/2005 |
| WO | WO 2005/112783 A1 | 12/2005 |
| WO | 2007/048085 A2 | 4/2007 |

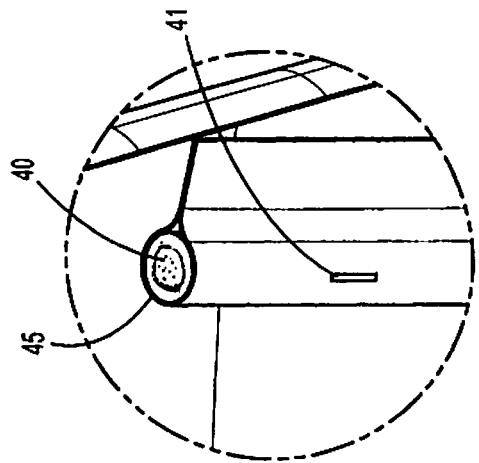
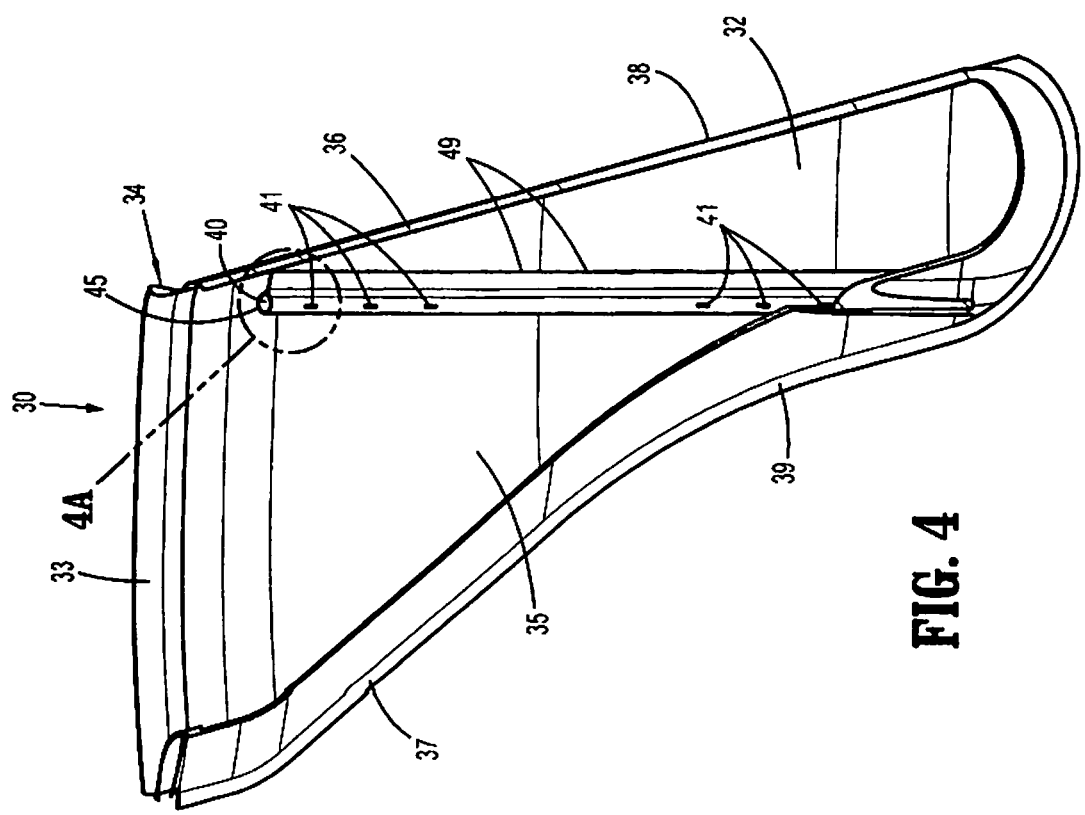

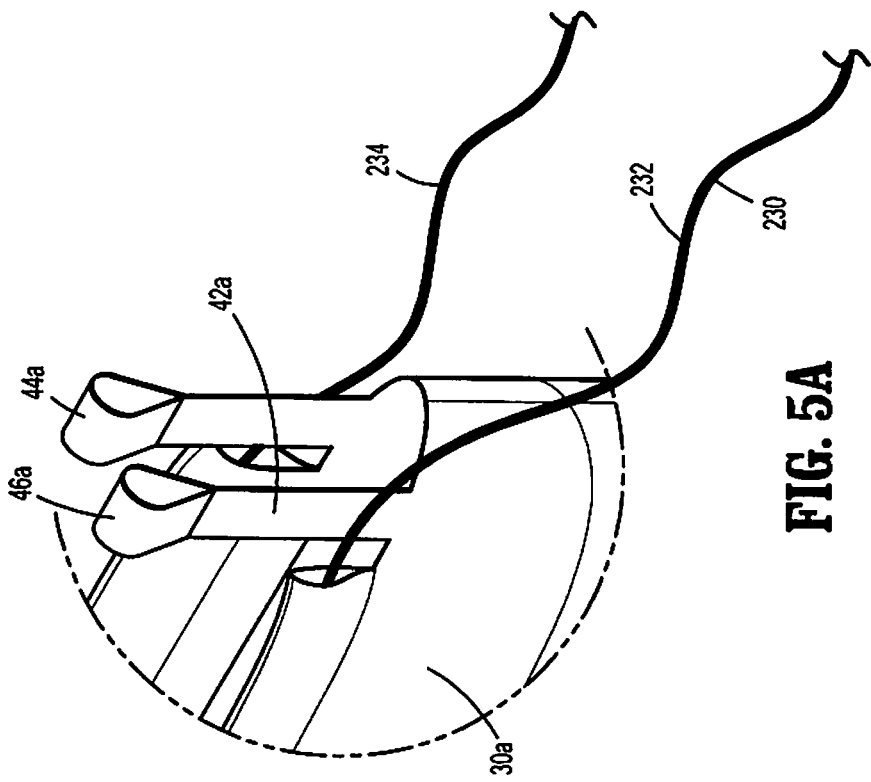
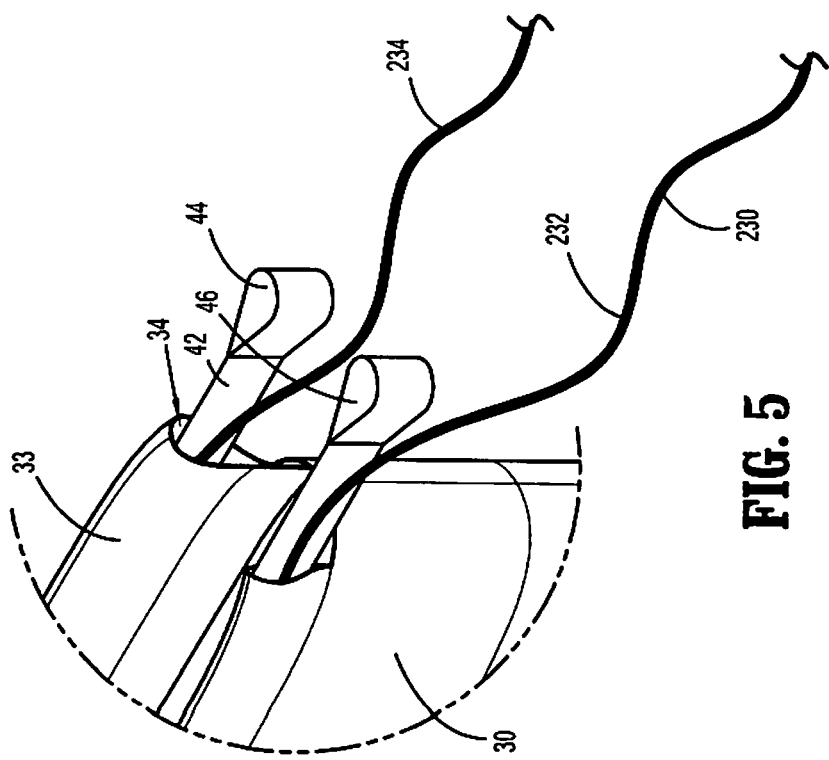

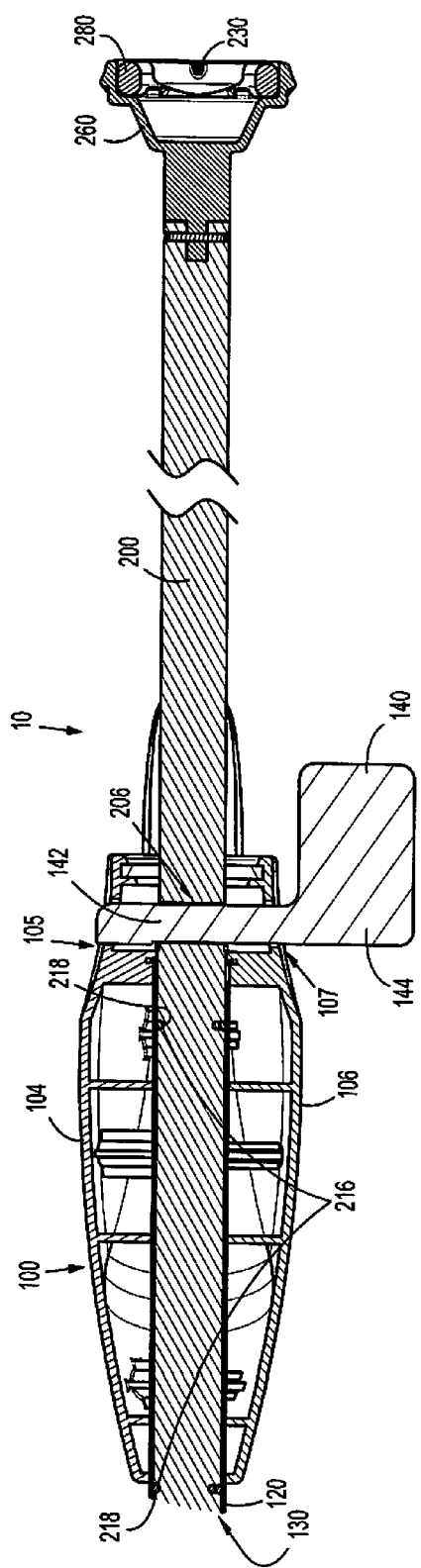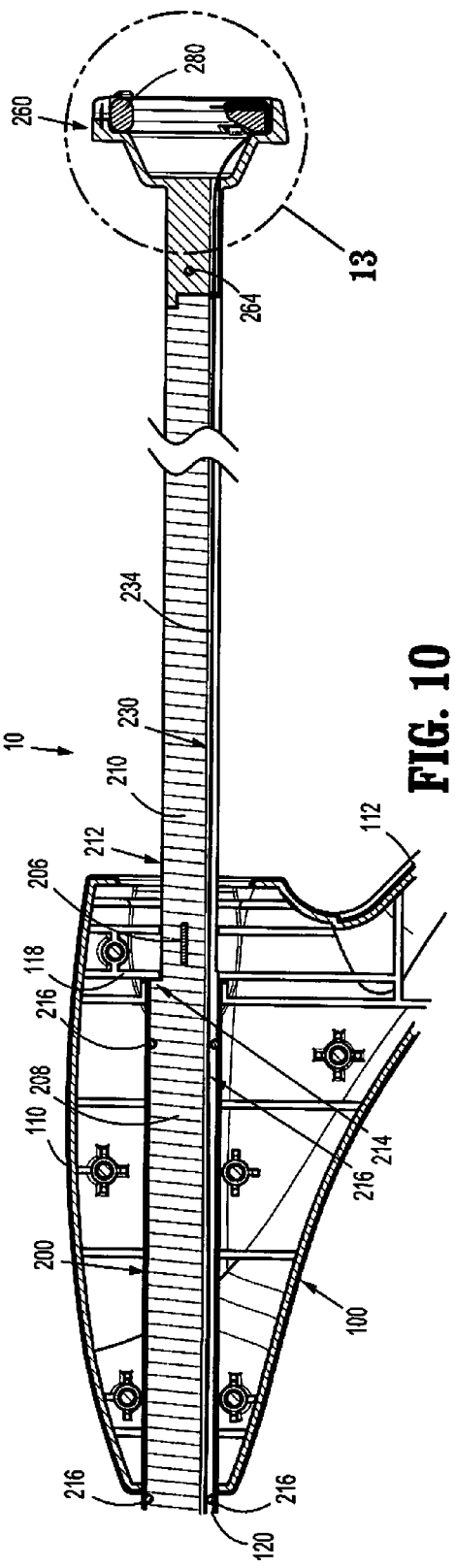

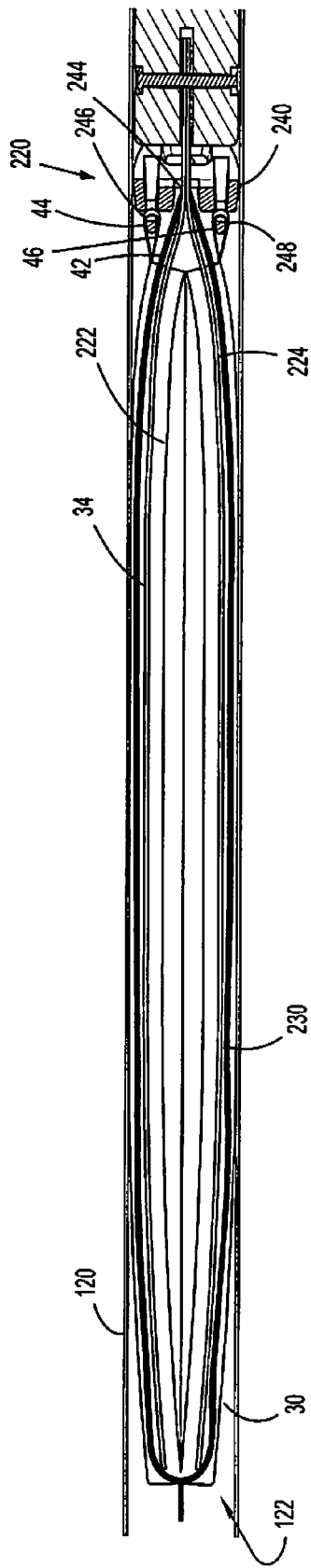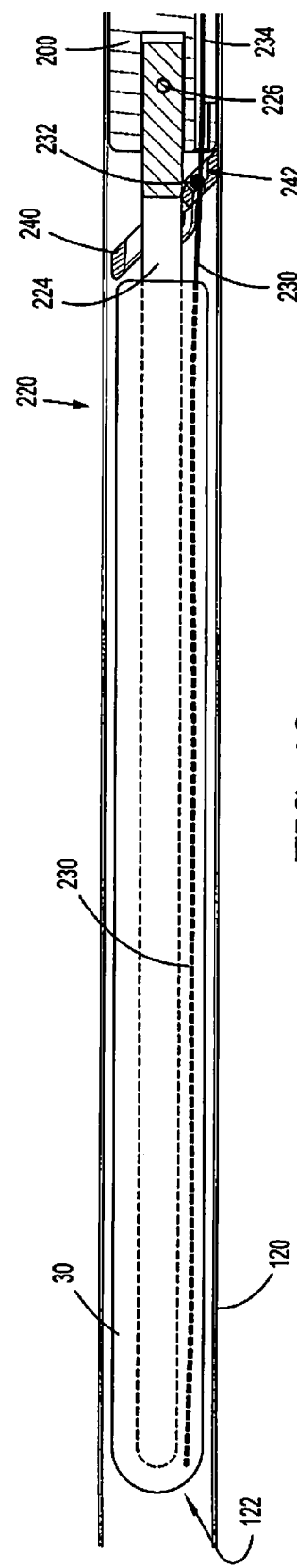
FIG. 11
FIG. 12

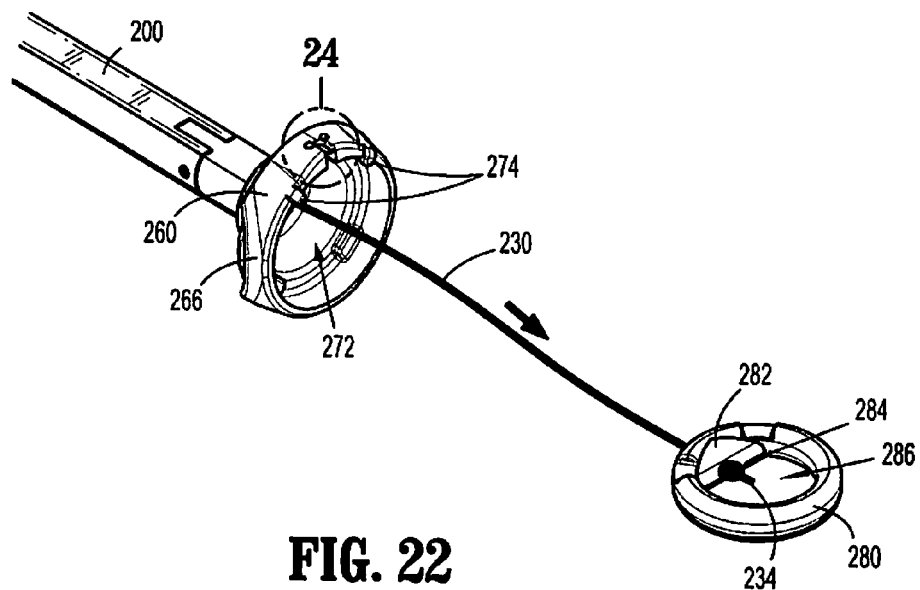
FIG. 22
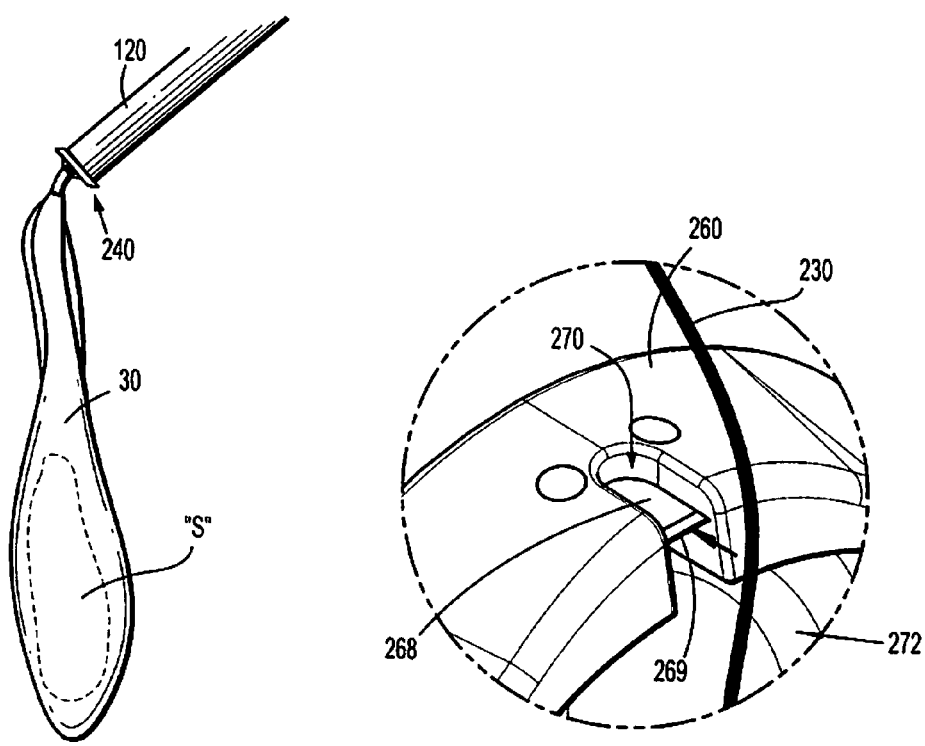
FIG. 23  FIG. 24

SURGICAL RETRIEVAL APPARATUS

This application claims priority from provisional application Ser. No. 61/499,923, filed Jun. 22, 2011, provisional application Ser. No. 61/430,206, filed Jan. 6, 2011 and provisional application Ser. No. 61/389,391, filed Oct. 4, 2010. The entire contents of each of these applications are incorporated herein by reference.

BACKGROUND

1. Technical Field

The present disclosure relates to a retrieval apparatus, and more particularly, to a surgical retrieval apparatus for use in minimally invasive surgical procedures.

2. Background of Related Art

In minimally invasive surgical procedures, operations are carried out within the body by using elongated instruments inserted through small entrance openings in the body. The initial opening in the body tissue to allow passage of instruments to the interior of the body may be a natural passageway of the body, or it can be created by a tissue piercing instrument such as a trocar, or created by a small incision into which a cannula is inserted.

Because the tubes, instrumentation, and any required punctures or incisions are relatively small, the surgery is less invasive as compared to conventional surgical procedures in which the surgeon is required to cut open large areas of body tissue. Therefore, minimally invasive surgery minimizes trauma to the patient and reduces patient recovery time and hospital costs.

Minimally invasive procedures may be used for partial or total removal of body tissue or organs from the interior of the body, e.g. nephrectomy, cholecystectomy, lobectomy and other procedures including thoracic, laparoscopic and endoscopic procedures. During such procedures, it is common that a cyst, tumor, or other affected tissue or organ needs to be removed via the access opening in the skin, or through a cannula. Various types of entrapment devices have been disclosed to facilitate this procedure. In many procedures where cancerous tumors are removed, removal of the specimen in an enclosed environment is highly desirable to inhibit seeding of cancer cells.

In minimally invasive thoracic surgery, access to the thoracic cavity is limited as well as maneuverability within the cavity as the access port is placed between the confined space between a patient's ribs. Such procedures, commonly referred to as video assisted thoracic surgery (VATS), aim to reduce patient recovery time by accessing the thoracic cavity through the natural intercostal space without spreading the ribs as in open procedures. This restricted access can sometimes cause problems when removing large specimens. Moreover, in such procedures, e.g. thorascopic wedge resection and lobectomy, it is often necessary to remove a portion of the lung and retrieve it relatively intact for pathology. It is also important that the specimen be sufficiently contained to inhibit seeding of cancer cells during manipulation and removal.

In designing such specimen retrieval instrumentation, a balance must be struck between the need to provide a retrieval apparatus with a strong enough containment bag to prevent tearing or rupture while providing sufficient rigidity to enable manipulation and removal. Another balance which needs to be achieved is to provide sufficient maneuverability while reducing tissue trauma, e.g. damaging lung tissue, during manipulation and removal. Additionally, the instrumentation on one hand should be able to be inserted through a small access incision or port while on the other hand able to accommodate a wide range of patient sizes and be able to easily remove large specimens and minimize risk of seeding.

SUMMARY

In accordance with embodiments of the present disclosure, a surgical retrieval apparatus is provided. In one aspect, the surgical retrieval apparatus includes a housing defining a longitudinal axis. The housing includes an elongated sleeve extending distally therefrom that, together with the housing, cooperates to define a lumen extending longitudinally therethrough. A shaft having an end effector assembly disposed at a distal end thereof is selectively translatable between a first position, wherein the end effector assembly is disposed within the elongated sleeve, and a second position, wherein the end effector assembly extends distally from the elongated sleeve. A specimen retrieval bag is releasably coupled to the end effector assembly and is deployable from an undeployed position to an extended position upon movement of the end effector assembly from the first position to the second position. A stop member is disposed between the end effector assembly and the shaft. The stop member is configured to inhibit the specimen retrieval bag from returning to within the lumen of the sleeve upon translation of the shaft from the second position back to the first position.

In some embodiments, the specimen retrieval bag includes a cinch cord disposed about an open end thereof and a pull-member is releasably coupled to the plunger and is coupled to the cinch cord, the pull-member configured, upon release from the plunger, for selective proximal translation to cinch closed the specimen retrieval bag.

The specimen retrieval bag may include a strap coupled thereto that is secured to the stop member.

In some embodiments, a channel extends within the specimen retrieval bag and extends along at least a portion of the length of the specimen retrieval bag wherein the channel is configured to evacuate air from the specimen retrieval bag. The conduit can include an open cell foam material positioned therein. The specimen retrieval bag in some embodiments includes a generally frustoconical configuration and a distal region of the specimen retrieval bag includes a generally rectilinear configuration.

In some embodiments, the shaft is manually translatable between the first and second positions. Translation of the shaft from the second position back to the first position may also at least partially cinch closed the specimen retrieval bag and/or separate the specimen retrieval bag from the end effector assembly.

A safety tab can be provided which is configured to engage both the housing and the shaft by being disposed through slots defined in both the shaft and housing when the shaft is disposed in the first position to inhibit relative movement between the housing and the shaft.

In some embodiments, a plunger is provided proximal of the shaft and is configured to mate with the housing when the shaft is disposed in the second position. The plunger may further include one or more flanges configured to facilitate translation of the shaft from the second position back to the first position, i.e., to facilitate separation of the plunger from mating relation with the housing. Additionally, the housing may include one or more detents positioned adjacent to the flanges of the plunger to further facilitate translation of the shaft from the second position back to the first position.

In some embodiments, the plunger includes one or more resilient lock tabs configured to releasably engage the pull-member thereon. The plunger may also include a blade engaged thereto that is configured to facilitate cutting of the cinch cord to disengage the specimen retrieval bag from the instrument. Further, the blade may be disposed within a recess defined within the plunger, i.e., such that the blade is not exposed, to inhibit damage and/or injury upon contacting the outer surface of the plunger.

In some embodiments, the shaft includes a shoulder defined on an outer periphery thereof configured to inhibit translation of the shaft proximally of the first position. The shaft may also include one or more O-rings disposed thereabout that are configured to frictionally retain the shaft in position relative to the housing and the elongated sleeve.

In some embodiments, the end effector assembly includes a pair of arms configured to receive the specimen bag thereon, the arms separable from the bag after closing the bag and withdrawal of the shaft. The arms preferably extend through on opening in the stop member. A diameter of the shaft in preferred embodiments is larger than a diameter of the opening in the stop member to prevent proximal movement of the stop member over the shaft. The stop member in some embodiments is configured to pivot when advanced from the shaft to prevent retraction into the shaft. The cinch cord and strap can extend through the stop member.

In another aspect, a surgical retrieval apparatus is provided comprising a housing defining a longitudinal axis and including an elongated sleeve extending distally therefrom, the housing and the elongated sleeve cooperating to define a lumen extending longitudinally therethrough. A shaft has an end effector assembly disposed at a distal end thereof and a plunger disposed at a proximal end thereof, the shaft selectively translatable between a first position, wherein the end effector assembly is disposed within the elongated sleeve, and a second position, wherein the end effector assembly extends distally from the elongated sleeve. A specimen retrieval bag is releasably coupled to the end effector assembly, the specimen retrieval bag deployable from an undeployed position to an extended position upon movement of the end effector assembly from the first position to the second position. The specimen retrieval bag includes a cinch cord disposed about an open end thereof and further includes a channel extending longitudinally therein for evacuation of air from the channel.

In some embodiments, the specimen retrieval bag includes a generally frustoconical configuration and a distal region of the specimen retrieval bag includes a generally rectilinear configuration. The specimen retrieval bag can include an open cell material positioned in the channel, which in some embodiments is compressible. In some embodiments, the housing includes a pistol grip. In some embodiments, the plunger is movable to a distal position to mate with the housing and to be substantially flush with the housing. In some embodiments, the end effector assembly includes a pair of arms configured to receive the specimen retrieval bag thereon, the arms separable from the bag after closing the bag and withdrawal of the shaft.

BRIEF DESCRIPTION OF THE DRAWINGS

Various embodiments of the subject surgical retrieval apparatus are described herein with reference to the drawings wherein:

FIG. 4 is a side, cut-away view of a specimen retrieval bag configured for use with the surgical retrieval apparatus of FIG. 1;

FIG. 4A is an enlarged view of the area of detail of FIG. 4;

FIG. 5 is an enlarged, perspective view of a proximal end of the specimen retrieval bag of FIG. 4;

FIG. 5A is an enlarged, perspective view of an alternate embodiment of the proximal end of the specimen retrieval bag;

FIG. 9 is an enlarged, top, longitudinal cross-sectional view of a proximal end of the surgical retrieval apparatus of FIG. 1, shown in the retracted position;

FIG. 10 is an enlarged, side, longitudinal cross-sectional view of the proximal end of the surgical retrieval apparatus of FIG. 1, shown in the retracted position;

FIG. 11 is an enlarged, top, longitudinal cross-sectional view of a distal end of the surgical retrieval apparatus of FIG. 1, shown in the retracted position;

FIG. 12 is an enlarged, side, longitudinal cross-sectional view of the distal end of the surgical retrieval apparatus of FIG. 1, shown in the retracted position;

FIG. 22 is a side, perspective view of the base of the plunger of FIG. 13, wherein a ring member thereof has been retracted to cinch the specimen retrieval bag closed;

FIG. 23 is a side view of the distal end of the surgical retrieval apparatus of FIG. 1, wherein the specimen retrieval bag has been cinched closed;

FIG. 24 is a greatly enlarged, perspective view of the base of the plunger of FIG. 13 showing a blade disposed thereon and configured to cut a cinch cord of the surgical retrieval apparatus;

DETAILED DESCRIPTION

Figure 1:
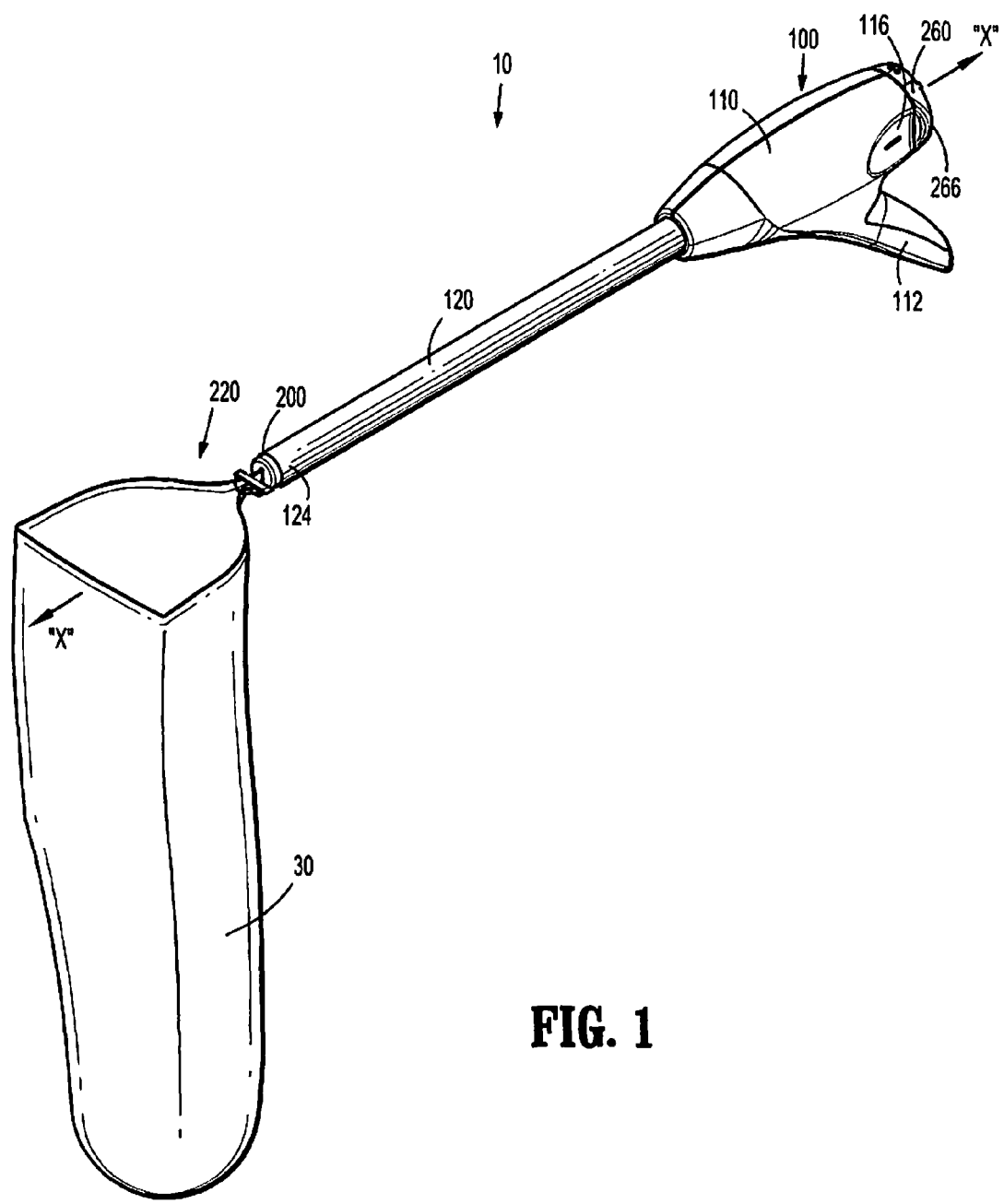
FIG. 1 is a side, perspective view of one embodiment of a surgical retrieval apparatus in accordance with the present disclosure, shown in a deployed (extended) position.

Various embodiments of the presently disclosed surgical retrieval apparatus, and methods of using the same, will now be described in detail with reference to the drawings wherein like references numerals identify similar or identical elements. In the drawings, and in the following description, the term "proximal" should be understood as referring to the end of the apparatus, or component thereof, that is closer to the clinician during proper use, while the term "distal" should be understood as referring to the end that is farther from the clinician, as is traditional and conventional in the art.

Although the presently disclosed surgical retrieval apparatus is discussed with respect to minimally invasive thoracic procedures, it is within the scope of the present disclosure that the surgical retrieval apparatus is readily adaptable for use in other minimally invasive surgical procedures such as laparoscopic procedures.

Figure 2:
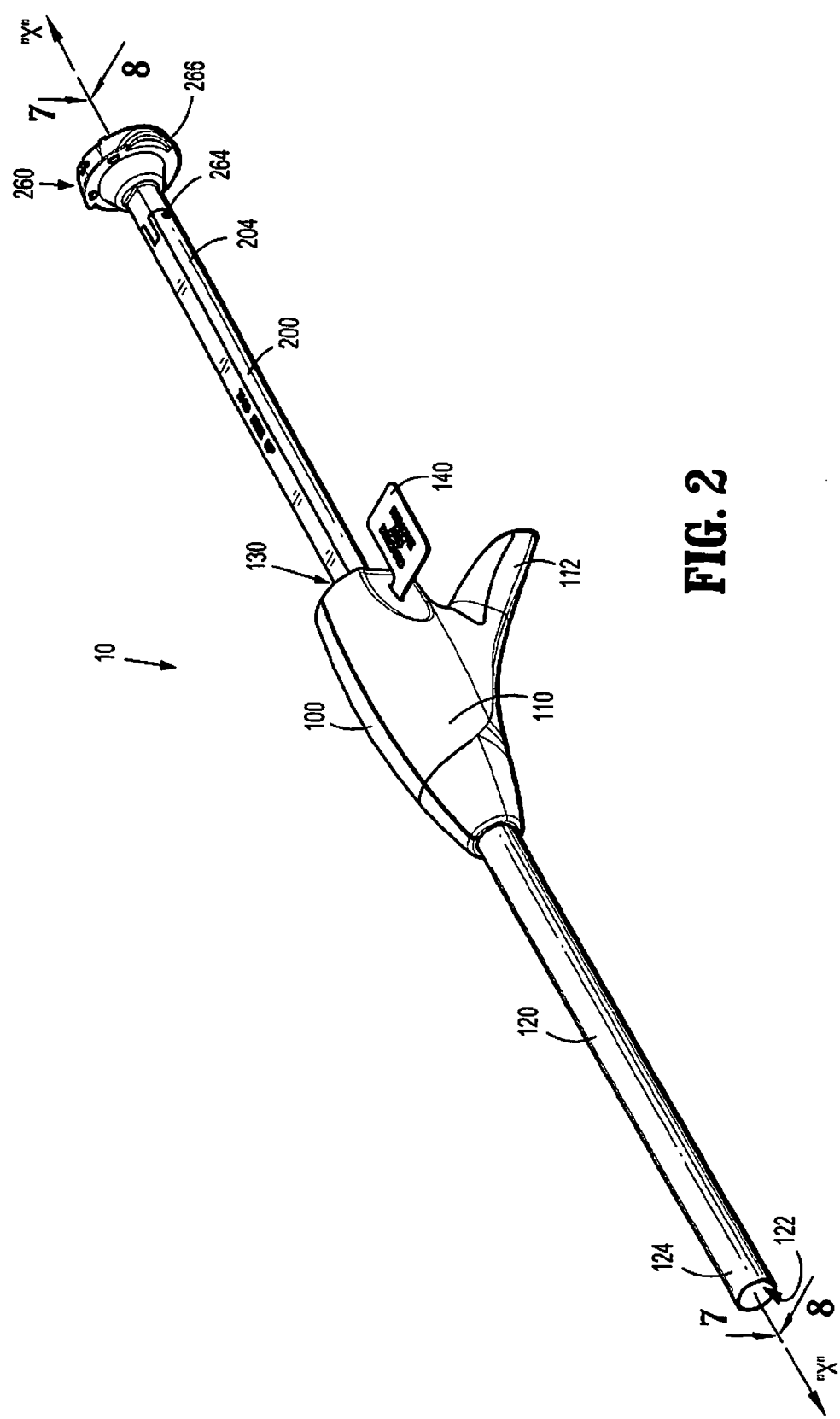
FIG. 2 is a side, perspective view of the surgical retrieval apparatus of FIG. 1, shown in a retracted (insertion/removal) position.
Figure 3:
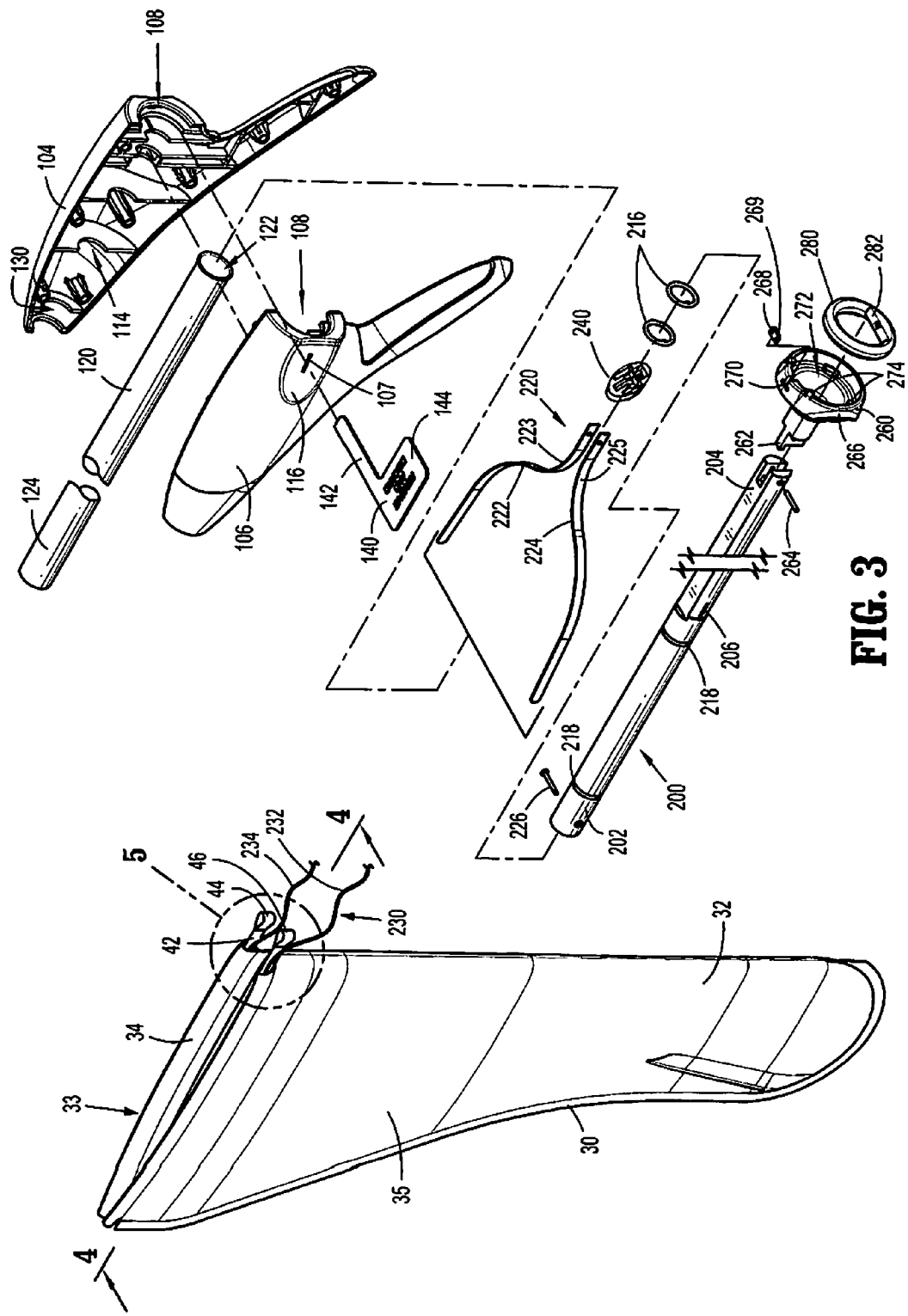
FIG. 3 is an exploded, perspective view of the surgical retrieval apparatus of FIG. 1.

Turning now to FIGS. 1-3, a surgical retrieval apparatus in accordance with the present disclosure is shown generally identified by reference numeral 10. Surgical retrieval apparatus 10 generally includes a housing 100 having an elongated sleeve 120 fixedly engaged thereto and extending distally therefrom, and a shaft 200 having an end effector assembly 220 disposed at a distal end 202 thereof. As will be described in detail below, shaft 200 and end effector assembly 220 are longitudinally translatable relative to housing 100 and elongated sleeve 120 to transition surgical retrieval apparatus 10 between a first, initial, insertion/removal, or retracted position (FIG. 2) and a second, extended, or deployed position (FIG. 1).

Housing 100 is formed from a pair of cooperating housing components 104, 106, e.g., via snap-fitting, and includes a body portion 110 and an ergonomically-designed handle portion 112 depending therefrom to facilitate grasping of surgical retrieval apparatus 10 by a clinician. More specifically, the configuration of handle portion 112 of housing 100 permits the clinician to grasp housing 100 in numerous configurations, while still being able to firmly grasp and fully manipulate and operate surgical retrieval apparatus 10. For example, the clinician may grasp housing 100 using a pistol grip, a palm grip, an upside-down grip, a rear grip, a front grip, etc. The specific grip used may depend on the clinician's preference or the surgical procedure being performed.

Body portion 110 of housing 100 and elongated sleeve 120 together define a longitudinal axis "X-X." More particularly, housing 100 defines a longitudinal passageway 114 extending through body portion 110 thereof and along longitudinal axis "X-X," and elongated sleeve 120 defines a lumen 122 extending longitudinally therethrough that is centered about longitudinal axis "X-X." Passageway 114 and lumen 122 cooperate with one another to define a channel 130 disposed about longitudinal axis "X-X" and extending distally from proximal aperture 108 of housing 100, through body portion 110 of housing 100, and through elongated sleeve 120 to distal end 124 thereof, i.e., channel 130 extends completely through surgical retrieval apparatus 10 along longitudinal axis "X-X" thereof.

Elongated sleeve 120 is configured for insertion through an opening in tissue, e.g., through a thoracic surgical access portal 300 (FIG. 15) disposed within an incision "I" (FIG. 15) in tissue "T" (FIG. 15) between adjacent ribs "R" (FIG. 16) of a patient. As such, it is envisioned that elongated sleeve 120 define a sufficient length such that elongated sleeve 120 may be advanced into the thoracic cavity "C" (FIGS. 16 and 18) to a position adjacent a tissue specimen "S" (FIG. 18) to be removed, while housing 100 remains external of the patient. Further, it is envisioned that elongated sleeve 120 define a diameter sufficiently large to permit passage of end effector assembly 220 and shaft 200 therethrough, but sufficiently small such that elongated sleeve 120 may be inserted between adjacent ribs "R" (FIG. 16) of a patient, i.e., through thoracic access portal 300 (FIG. 15) disposed within an incision "I" (FIG. 15) in the intercostal space.

Shaft 200 includes an end effector assembly 220 disposed at a distal end 202 thereof and is slidably positionable within channel 130. Shaft 200 is longitudinally translatable between the retracted position (FIG. 2), wherein shaft 200 is retracted proximally relative to housing 100 and elongated sleeve 120 such that end effector assembly 220 is disposed within channel 130, i.e., such that end effector assembly 220 does not extend from distal end 124 of sleeve 120, and the deployed position (FIG. 1), wherein shaft 200 is translated distally through channel 130 such that end effector assembly 220 extends distally from distal end 124 of elongated sleeve 120 to deploy specimen retrieval bag 30.

With continued reference to FIGS. 1-3, shaft 200 includes a plunger 260 disposed at proximal end 204 thereof. More specifically, shaft 200 includes a bifurcated proximal end 204 and plunger 260 includes a protrusion 262 extending therefrom that is configured to be received within the bifurcated proximal end 204 of shaft 200. A pin 264 inserted through each of the bifurcated portions of proximal end 204 of shaft 200 and through protrusion 262 of plunger 260 secures plunger 260 to proximal end 204 of shaft 200. As best shown in FIG. 1, plunger 260 is configured to mate with housing 100 when shaft 200 is disposed in the deployed position so as not to extend substantially proximally therefrom in preferred embodiments is substantially flush with the proximal end of housing 100. Such a configuration inhibits catching of plunger 260 on the clinician's clothing, interference with other surgical instrumentation, and/or inadvertent movement of shaft 200 relative to housing 100 and elongated sleeve 120. In the deployed position, flanges 266 of plunger 260, which extend from opposed sides of plunger 260, cooperate with detents 116 defined within opposed sides of housing 100 to provide a grasping region to facilitate the grasping of flanges 266 to retract plunger 260 and, thus, shaft 200 relative to housing 100 and elongated sleeve 120, e.g., from the deployed position (FIG. 1) back to the retracted position (FIG. 2).

Plunger 260 further includes a pull-ring 280 that is removably disposed therein and a blade 268 for cutting cinch cord 230, as will be described greater detail below. Blade 268 is disposed within a recess 270 defined within plunger 260 such that sharpened edge 269 of blade 268 is not exposed to clothing, instrumentation, or tissue that contacts the outer surface of plunger 260. Pull-ring 280 is coupled to cinch cord 230 of specimen retrieval bag 30 and includes a lip 282 extending inwardly therefrom that facilitates the grasping of pull-ring 280 for disengaging pull-ring 280 from plunger 260 and retracting pull-ring 280 relative to plunger 260 to tension cinch cord 230. More specifically, pull-ring 280 is releasably engagable within recessed proximal portion 272 of plunger 260 via a plurality of resilient lock tabs 274. A more detailed description of pull-ring 280, including the operation thereof, will be described hereinbelow.

As shown in FIGS. 2-3, housing 100 and shaft 200 may both be configured to receive a safety tab 140 therethrough to inhibit accidental or premature deployment of shaft 200 and specimen retrieval bag 30. More specifically, safety tab 140 is configured to extend through slot 105 (FIG. 9) defined within housing component 104, slot 206 extending through shaft 200 and slot 107 defined within housing component 106 to maintain housing 100 and shaft 200 in substantially fixed position relative to one another, thereby inhibiting translation of shaft 200 relative to housing 100 to deploy and/or retract end effector assembly 220 and specimen retrieval bag 30.

Figure 6:
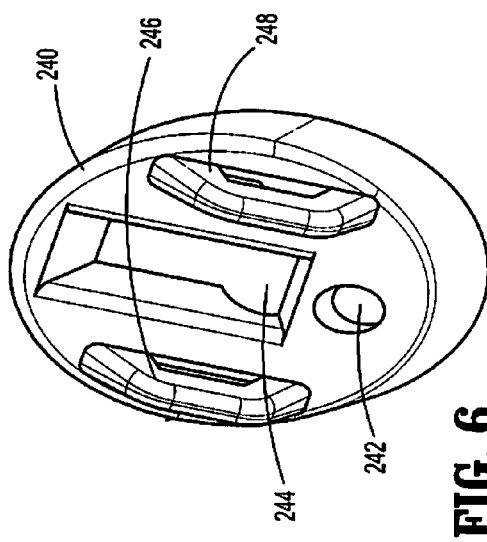
FIG. 6 is a front, perspective view of a stop member configured for use with the surgical retrieval bag of FIG. 1.
Figure 7:
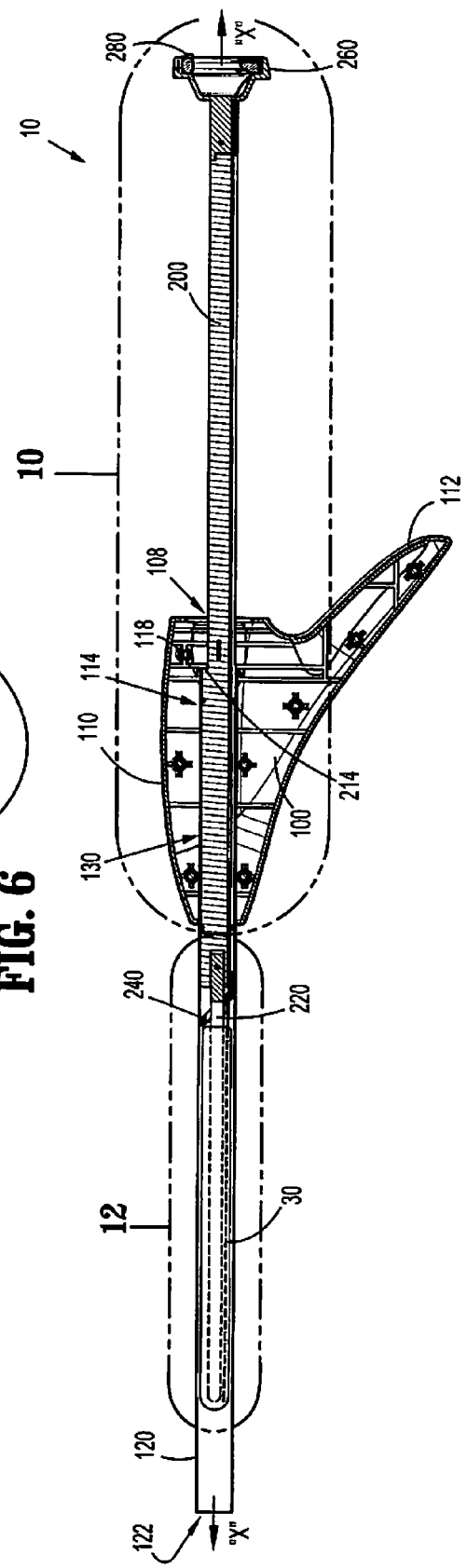
FIG. 7 is a side, longitudinal cross-sectional view of the surgical retrieval apparatus of FIG. 1, shown in the retracted position.

Referring now to FIGS. 4-6, in conjunction with FIG. 3, specimen retrieval bag 30 is removably coupled to end effector assembly 220 and depends therefrom. More specifically, specimen retrieval bag 30 is folded over at an open end 33 thereof to form a loop 34 or channel around the outer periphery thereof adjacent the mouth of the bag 30. End effector assembly 220 includes a pair of arms 222, 224 configured for removable positioning within loop 34 formed at open end 33 of specimen retrieval bag 30 to retain specimen retrieval bag 30 thereon. In the deployed position, as shown in FIG. 1, arms 222, 224 of end effector assembly 220 define a spaced-apart, curvate configuration for retaining specimen retrieval bag 30 thereon in an open condition, although other configurations are also contemplated, e.g., end effector assembly 220 may include linear arms 222, 224. In the retracted position, on the other hand, arms 222, 224 of end effector assembly 220 are disposed in a substantially-straight configuration in close proximity to one another to permit positioning within and translation through lumen 122 of elongated sleeve 120. As will be described below, arms 222, 224 may be biased toward the spaced-apart, curvate configuration such that upon exposure from elongated sleeve 120, arms 222, 224 are automatically deployed, i.e., arms 222, 224 are resiliently returned, to the spaced-apart curvate configuration, thus transitioning specimen retrieval bag 30 to the open condition.

Continuing with reference to FIGS. 4-6, in conjunction with FIG. 3, as will be described in greater detail below, a cinch cord 230 is disposed through loop 34 of specimen retrieval bag 30. First and second ends 232, 234, respectively, of cinch cord 230 extend proximally from loop 34 of specimen retrieval bag 30 through cinch cord aperture 242 defined within stop member 240 disposed at distal end 202 of shaft 200. One of the ends, e.g., first end 232, is knotted, or otherwise secured adjacent cinch cord aperture 242 on the proximal side thereof and may be looped about second end 234 thereof (see FIG. 19), while the other end, e.g., second end 234, extends proximally though shaft 200, ultimately engaging, i.e., knotting about, pull-ring 280. Accordingly, as will be described in greater detail below, upon translation of pull-ring 280 proximally relative to shaft 200, cinch cord 230 is likewise pulled proximally to tension cinch cord 230 such that specimen retrieval bag 30 is cinched closed.

End effector assembly 220 further includes a stop member 240 disposed at distal end 202 of shaft 200. Stop member 240 includes a generally-rectangular opening 244, although other configurations are contemplated, that is configured to receive arms 222, 224 of end effector assembly 220 therethrough. More particularly, arms 222, 224 of end effector assembly 220 are engaged to shaft 200 at proximal ends 223, 225, respectively, thereof via pin 226, and extend distally therefrom through opening 244 of stop member 240. Stop member 240 is retained on arms 222, 224 of end effector assembly 220 between shaft 200 and the curvate portions of arms 222, 224. In other words, with arms 222, 224 extending through opening 244 of stop member 240, stop member 240 is retained on end effector assembly 220 in that stop member 240 is inhibited from passing proximally over shaft 200 due to diameter of shaft 200, which is larger than the diameter of opening 244, and is likewise inhibited from passing distally over arms 222, 224 due to the biasing of arms 222, 224, outwardly from one another to define a distance therebetween that is greater than the diameter of opening 244 of stop member 240.

Stop member 240 also includes, as mentioned above, a cinch cord aperture 242 configured to permit passage of first and second ends 232, 234, respectively, of cinch cord 230 therethrough and to inhibit distal translation of knotted first end 232 of cinch cord 230 therethrough. Further, a pair of supports 246, 248 extends distally from the distal surface of stop member 240 on either side of opening 244. Supports 246, 248 are each configured to receive one of the looped ends 44, 46 of strap 42 of specimen retrieval bag 30 to retain specimen retrieval bag 30 thereon. Strap 42 extends through loop 34 of specimen retrieval bag 30, or is otherwise secured to specimen retrieval bag 30 such that looped ends 44, 46 may be used to secure specimen retrieval bag 30 to supports 246, 248, respectively, of stop member 240, which will be described in greater detail below.

As will be described in greater detail below, stop member 240 is initially disposed within elongated sleeve 120 when shaft 200 is in the retracted position. It is preferably disposed at an angled position as shown in FIG. 12. Upon deployment of end effector assembly 220, i.e., upon translation of shaft 200 to the deployed position, stop member 240 extends, along with end effector assembly 220, distally from elongated sleeve 120. However, due to the configuration of stop member 240, as will be described below, stop member 240 is inhibited from returning into lumen 122 of elongated sleeve 120, thus inhibiting specimen retrieval bag 30 from returning into lumen 122 of sleeve 120, while permitting arms 222, 224 of end effector assembly 220 to translate through opening 244 and back into lumen 122 of sleeve 120.

With continued reference to FIGS. 4-6, in conjunction with FIG. 3, it is envisioned that specimen retrieval bag 30 be formed from any suitable bio-compatible material (or materials), e.g., 30 Denier Ripstop Nylon, configured to retain a tissue specimen "S" (FIG. 18) therein and to inhibit the passage of fluids and biological materials therethrough. The bag 30 can include a coating, such as a polyurethane coating, to prevent egress of fluid if a permeable bag is utilized or to improve the impermeability. The coating can be placed on the inner surface and/or the outer surface of the bag 30. The bag 30 can also be formed with a thin urethane sheet to facilitate holding the edges of the bag material to form the bag. As shown in FIGS. 3 and 4, specimen retrieval bag 30 includes a lower portion 32 having a minimized cross-section configured to re-orient or re-position the specimen of tissue "S" (FIG. 18) within specimen retrieval bag 30 to facilitate removal of specimen retrieval bag 30 from an internal body cavity, and a relatively expansive upper portion 35 configured to facilitate positioning of relatively large specimen of tissue "S" (FIG. 18) within specimen retrieval bag 30. In other words, lower portion 32 has a smaller transverse dimension than upper portion 35. More specifically, upper portion 35 of specimen retrieval bag 30 has a generally straight first side 36 and a generally-angled side 37 disposed opposite first side 36. Angled side 37 tapers inwardly such that the transverse dimension of upper portion 35 of specimen retrieval bag 30 progressively decreases toward the lower portion 32 of specimen retrieval bag 30. Side 37 can be substantially linear or alternatively have a curved edge. Wall 38, which opposes wall 39 in lower portion 32 of specimen retrieval bag 30, extends substantially parallel to wall 39 such that the transverse dimension of lower portion 32 remains substantially constant along a length thereof until curved wall 39a at the lower portion 32. Alternatively, specimen retrieval bag 30 may be formed in various other configurations depending on the intended use of specimen retrieval bag 30.

As mentioned above, open end 33 of upper portion 35 of specimen retrieval bag 30 includes a loop 33 defined about the outer periphery thereof. Loop 33 is configured to receive arms of end effector assembly 220, strap 42, and cinch cord 230 therethrough for retaining specimen retrieval bag 30 on end effector assembly 220, for securing specimen retrieval bag 30 to stop member 240, and for cinching, or closing specimen retrieval bag 30, respectively.

Specimen retrieval bag 30 may in some embodiments further include a high-friction mesh material disposed on an inner surface thereof to facilitate retention of the tissue specimen "S" (FIG. 18) therein. In other embodiments, the bag shape is relied on to retain the specimen "S" and a smooth inner surface is provided to enable easy passage of the tissue specimen "S" from the upper loading area, i.e., upper portion 35, of the bag 30 to the lower shaping region, i.e., lower portion 32, of the bag 30 during extraction.

Specimen retrieval bag 30 further includes, in preferred embodiments, a channel or conduit 45 formed therein. The channel 45 can be formed as integral with the bag material or alternatively can be in the form of a separate tube attached to the bag 30, e.g. attached to an inner surface at edge 49. The material for the channel can be the same as the bag material or another material. The channel 45 includes at least one opening or slot along its length to allow the passage of air into the channel 45. Preferably, a plurality of slots or openings 41 are provided spaced apart along a longitudinal axis of the channel 45 to enable communication between the air and/or fluid in the bag 30 and the interior of the channel 45. In FIG. 4, three lower slots 41 and three upper slots 41 are provided, thereby allowing passage of air from the lower portion 32 of bag 30 to upper portion 35, although a different number, configuration and/or spacing of slots is also contemplated. The channel 45 in some embodiments can also terminate at its distal end spaced from the bottom of the bag 30 to communicate at a distal opening with the interior of the bag 30 to provide another path for the escape of air. Further, the proximal end of channel 45, in some embodiments, may be open to communicate with the exterior of the bag 30, but preferably terminates within the bag as shown.

A support member (or support members) 40 may be disposed within specimen retrieval bag 30 to help inhibit collapse of the channel 45 and/or for biasing specimen retrieval bag 30 toward an open position upon deployment from surgical retrieval apparatus 10. Support member 40 may be formed from, for example, an open cell material such as open cell foam, or other suitable material that enables the passage of air and/or fluid therethrough, thus allowing air to escape specimen retrieval bag 30 upon collapse or compression of specimen retrieval bag 30 to reduce the internal pressure within specimen retrieval bag 30. The open cell material is preferably of a transverse cross-section less than the transverse cross-section of the channel 45. In this manner, air entering the channel 45 from the bag 30 can flow around the open cell foam material through the channel 45. Note that due to the open cell foam, the air can also flow through the open cell foam itself. This way, if the channel 45 collapses or is compressed during specimen retrieval, air (and fluid) can still escape. The escape of air is caused as the pressure is applied to the bag 30 during withdrawal through access port 300 (FIG. 15), or body opening. As the bag 30 is compressed, the air is forced proximally through the channel 45, exiting the open proximal end thereof or through upper slots 41. Thus, this decrease in pressure prevents balling of the specimen "S" (FIG. 25) at the bottom of the bag 30 and facilitates removal as the specimen can be contained in a sausage-like shape to ease removal through the incision. The bag can be folded at an angle to form a "V" and then rolled to take advantage of the length of the tabs to keep it elongated (air can escape while folding to further reduce its profile).

It should be appreciated that other bag shapes containing channels and open cell foam or other support material can be utilized, such as those disclosed in provisional application Ser. No. 61/430,206, filed Jan. 6, 2011 and provisional application Ser. No. 61/389,391, filed Oct. 4, 2010. The entire contents of each of these applications are incorporated herein by reference.

Turning now to FIGS. 7-25, the use and operation of surgical retrieval apparatus 10 will be described along with a more detailed description of the working components of surgical retrieval apparatus 10. Although described for thoracic procedures, the apparatus 10 can be used in a similar manner to remove tissue specimens in other minimally invasive procedures, such as laparoscopic procedures. Initially, with reference to FIGS. 7-14, surgical retrieval apparatus 10 is disposed in the retracted position, wherein shaft 200 extends proximally from housing 100 and wherein end effector assembly 220, stop member 240, and specimen retrieval bag 30 are disposed within lumen 122 of elongated sleeve 120.

As best shown in FIG. 10, shaft 200 includes a distal portion 208 defining a first diameter and a proximal portion 210 including a cut-out 212 such that proximal portion 210 defines a second diameter that is smaller than the first diameter of distal portion 208. Further, a proximally-facing shelf, or shoulder 214 is defined at the interface between proximal and distal portions 210, 208, respectively, of shaft 200. Shoulder 214 is configured to contact internal support 118 of housing 100 to inhibit further proximal translation of shaft 200 relative to housing 100 beyond the retracted position, i.e., to inhibit complete removal of shaft 200 from housing 100.

Figure 8:
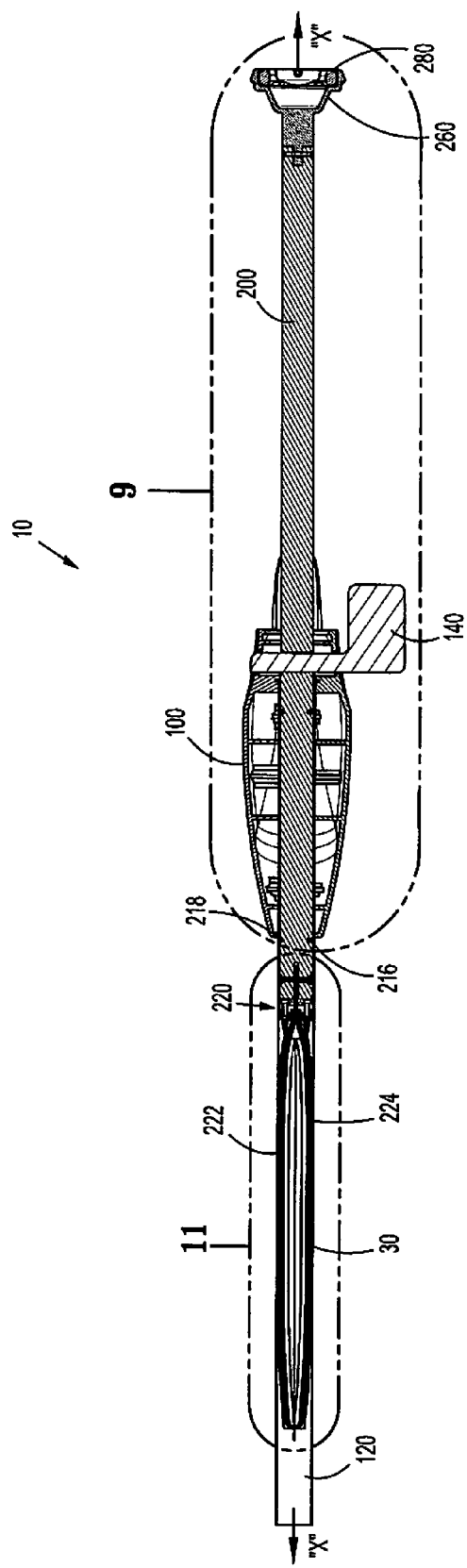
FIG. 8 is a top, longitudinal cross-sectional view of the surgical retrieval apparatus of FIG. 1, shown in the retracted position.
Figure 13:
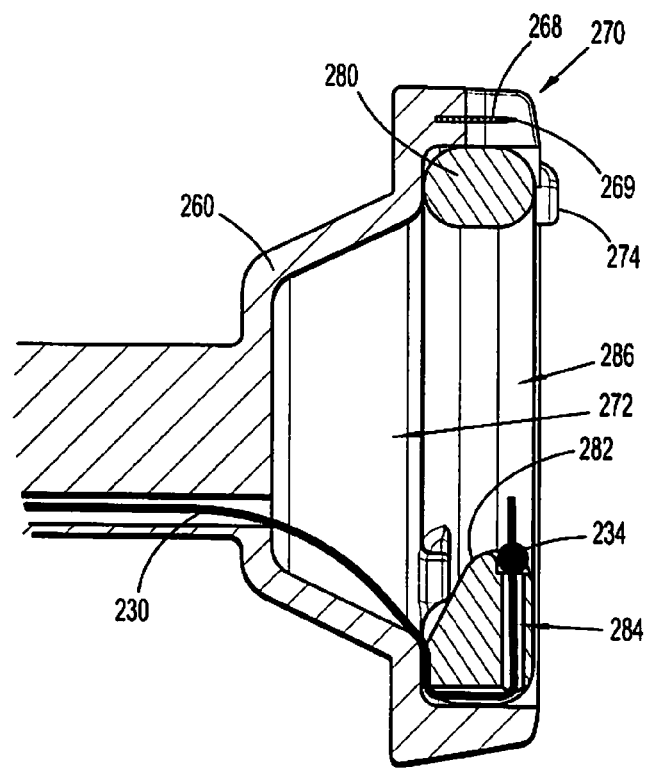
FIG. 13 is an enlarged, longitudinal cross-sectional view of a base of a plunger configured for use with the surgical retrieval apparatus of FIG. 1.
Figure 14:
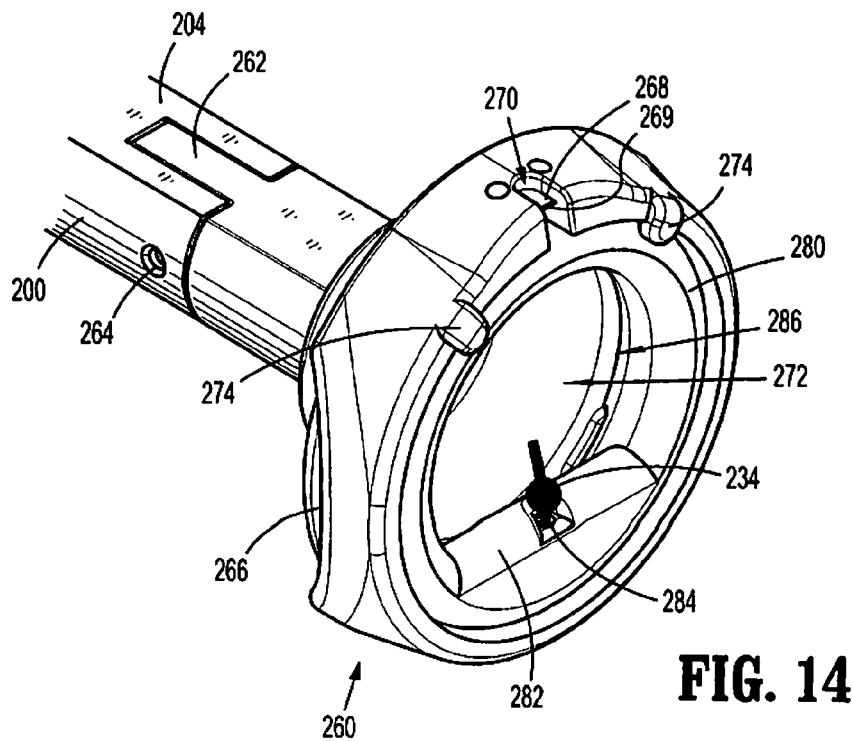
FIG. 14 is a side, perspective view of the base of the plunger of FIG. 13.

As best shown in FIGS. 8-10, shaft 200 includes one or more O-rings 216 spaced-apart along the length thereof. O-rings 216 may each be partially disposed within an annular groove 218 defined within the outer periphery of shaft 200 and are configured to extend radially outwardly therefrom to frictionally retain shaft 200 in position relative to housing 100 and elongated sleeve 120. As can be appreciated, such a configuration inhibits inadvertent translation of shaft 200 through housing 100 and elongated sleeve 120 in the absence of urging by the clinician, while permitting advancement of shaft 200 without significant resistance, i.e., without significantly increasing the force required to urge shaft 200 between the retracted and deployed positions. The O-ring can also provide a seal to prevent egress of fluids.

As mentioned above, and as shown in FIGS. 8 and 9, safety tab 140 extends through slot 105 defined within housing component 104, slot 206 extending through shaft 200, and slot 107 defined within housing component 106 to lock, or maintain housing 100 and shaft 200 in substantially fixed position relative to one another, thereby inhibiting undesired translation, e.g. during shipping, or handling, of shaft 200 relative to housing 100. More specifically, safety tab 140 includes a elongated portion 142 for insertion though slots 105, 206, 107 of housing components 104, shaft 200, and housing component 106, respectively, and an external grasping portion 144 to facilitate grasping by the clinician for removal of safety tab 140 from housing 100 and shaft 200, thus unlocking, or disengaging housing 100 and shaft 200 from a fixed position relative to one another.

Continuing with reference to FIGS. 7-14 and to FIGS. 11-12 in particular, in the retracted position, the internal dimensions of lumen 122 of elongated sleeve 120 retain arms 222, 224 of end effector assembly 220 therein in the substantially-straight, approximated position with specimen retrieval bag 30 rolled-up, or wrapped about arms 222, 224. Stop member 240 is likewise positioned within lumen 122 of elongated sleeve 120 and is disposed at an oblique angle relative thereto to permit disposition of stop member 240 therein. In this position, looped ends 44, 46 of strap 42 (see also FIG. 5), which is disposed through loop 34 of specimen retrieval bag 30, are engaged to supports 246, 248 of stop member 240, while first and second ends 232, 234 of cinch cord 230 extend from either end of loop 34 of specimen retrieval bag 30 and through cinch cord aperture 242 of stop member 240.

In the alternate embodiment of FIG. 5A, the straps 42a are integral with the bag and looped ends 44a, 46a extend upwardly as shown. The ends 44a, 46a are bent to a more horizontal position to engage supports 246, 248 of stop 240 in the same manner as looped ends 44, 46 of strap 42.

Referring now to FIGS. 11-14, first and second ends 232, 234, respectively, of cinch cord 230, as mentioned above, extend through cinch cord aperture 242 of stop member 240. More specifically, first end 232 of cinch cord 230 is knotted on a proximal side of stop member 240 and is looped about second end 234 (see FIG. 19), while second end 234 of cinch cord 230 extends through shaft 200, ultimately engaging pull-ring 280, e.g., passing through an aperture 284 defined within pull-ring 280 and knotting on a proximal side thereof. Pull-ring 280 is initially engaged within plunger 260 and, thus, cinch cord 230 is relatively un-tensioned. More specifically, pull-ring 280 is retained within recessed proximal portion 272 of plunger 260 via resilient lock tabs 274.

Figure 15:
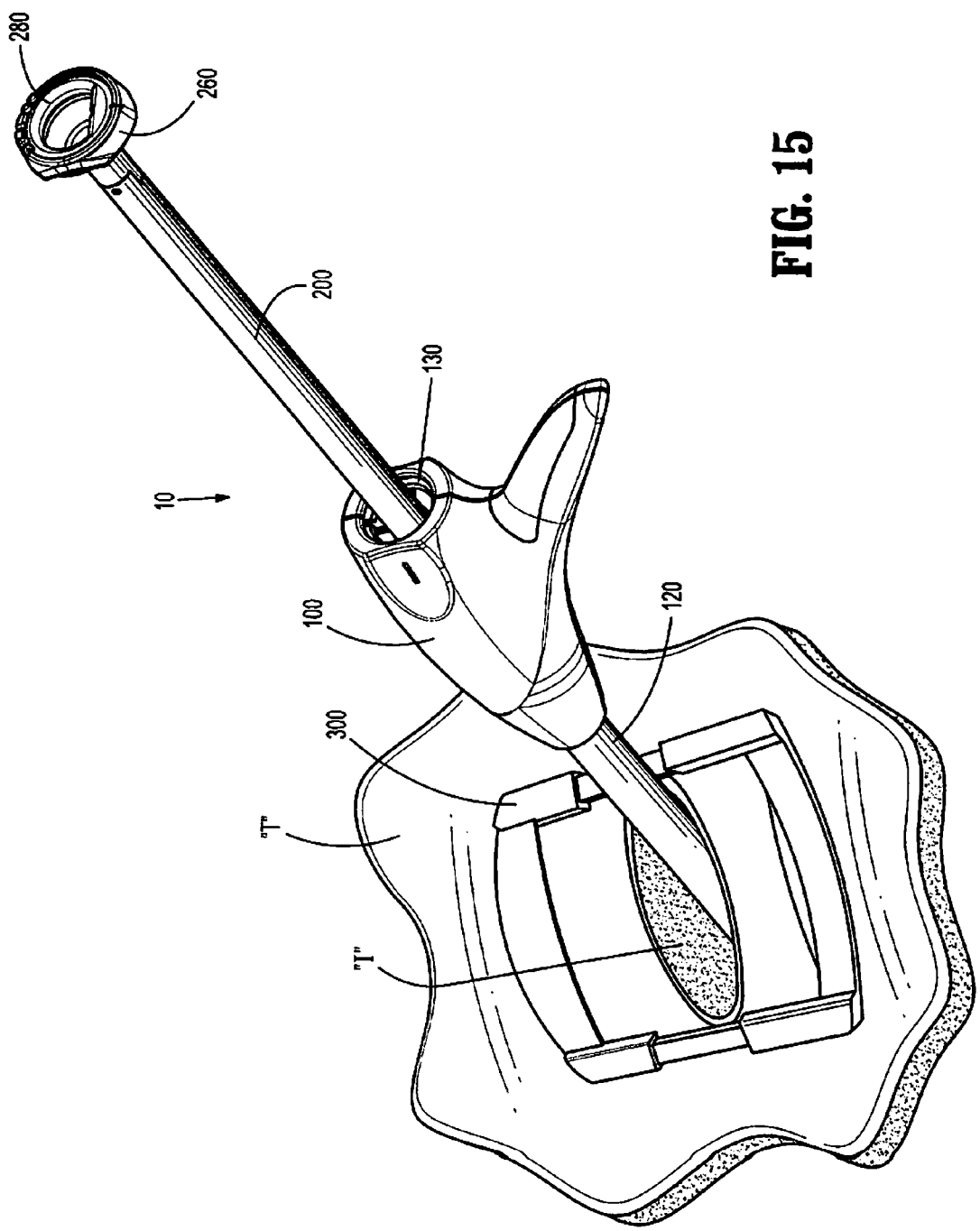
FIG. 15 is a side, perspective view of the surgical retrieval apparatus of FIG. 1, shown being inserted through an incision in tissue.
Figure 16:
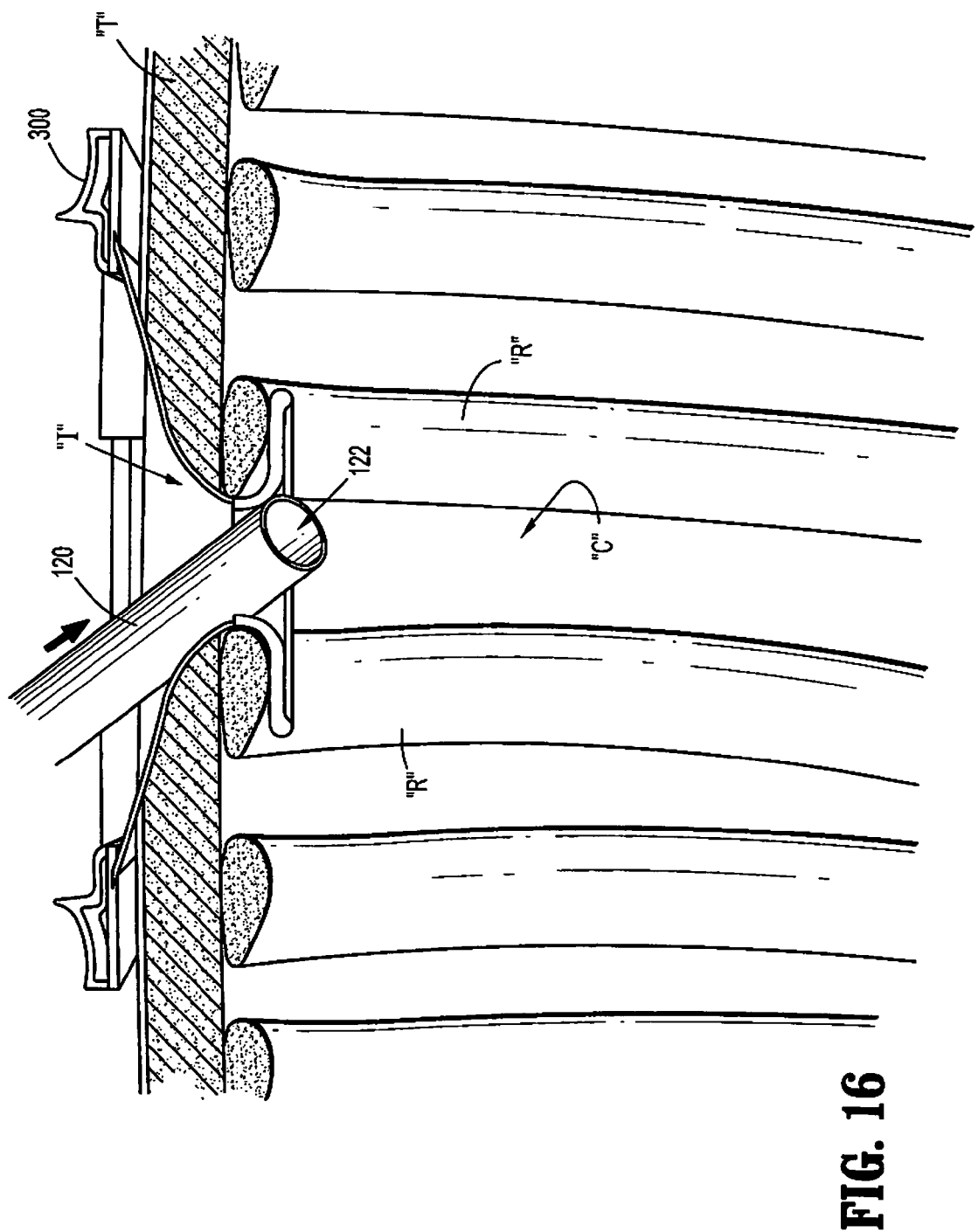
FIG. 16 is a transverse, cross-sectional view showing the surgical retrieval apparatus of FIG. 15 being inserted through an incision in tissue and into an internal surgical site (e.g., the thoracic cavity)

Turning now to FIGS. 15-16, in conjunction with FIGS. 1-14, in preparation for use, and with surgical retrieval apparatus 10 disposed in the retracted position, safety tab 140 is removed, although shaft 200 remains disposed in the retracted position via the frictional engagement between O-rings 216 and the inner surface of housing 100 defined by passageway 114. Next, surgical retrieval apparatus 10, lead by elongated sleeve 120, is inserted through thoracic access portal 300 positioned within an incision "I" in tissue "T" between adjacent ribs "R" of a patient, although surgical retrieval apparatus 10 may be directly inserted through the incision "I," or may be used in conjunction with any other suitable thoracic access portal (not shown). As can be appreciated, in this retracted position, since end effector assembly 220 does not extend from elongated sleeve 120, surgical retrieval apparatus 10 defines a reduced diameter to facilitate passage of elongated sleeve 120 through access portal 300, between adjacent ribs "R" of the patient, and into the internal surgical site, e.g., the thoracic cavity "C."

Figure 17:
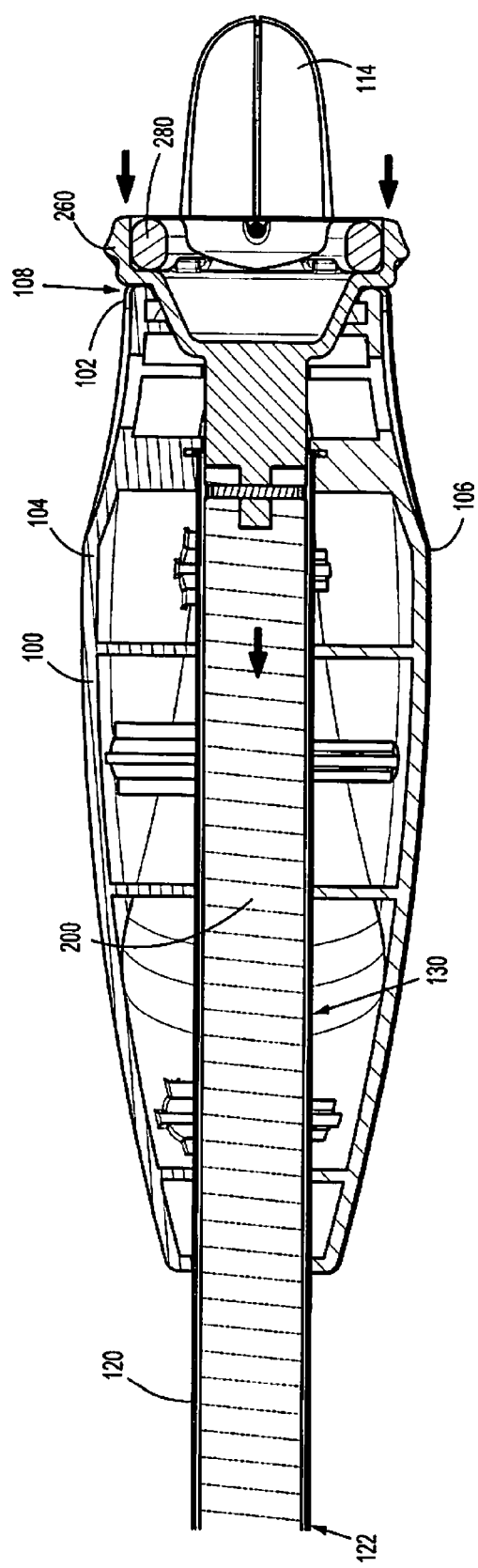
FIG. 17 is an enlarged, top, longitudinal cross-sectional view of the proximal end of the surgical retrieval apparatus of FIG. 1, shown in the deployed position.
Figure 18:
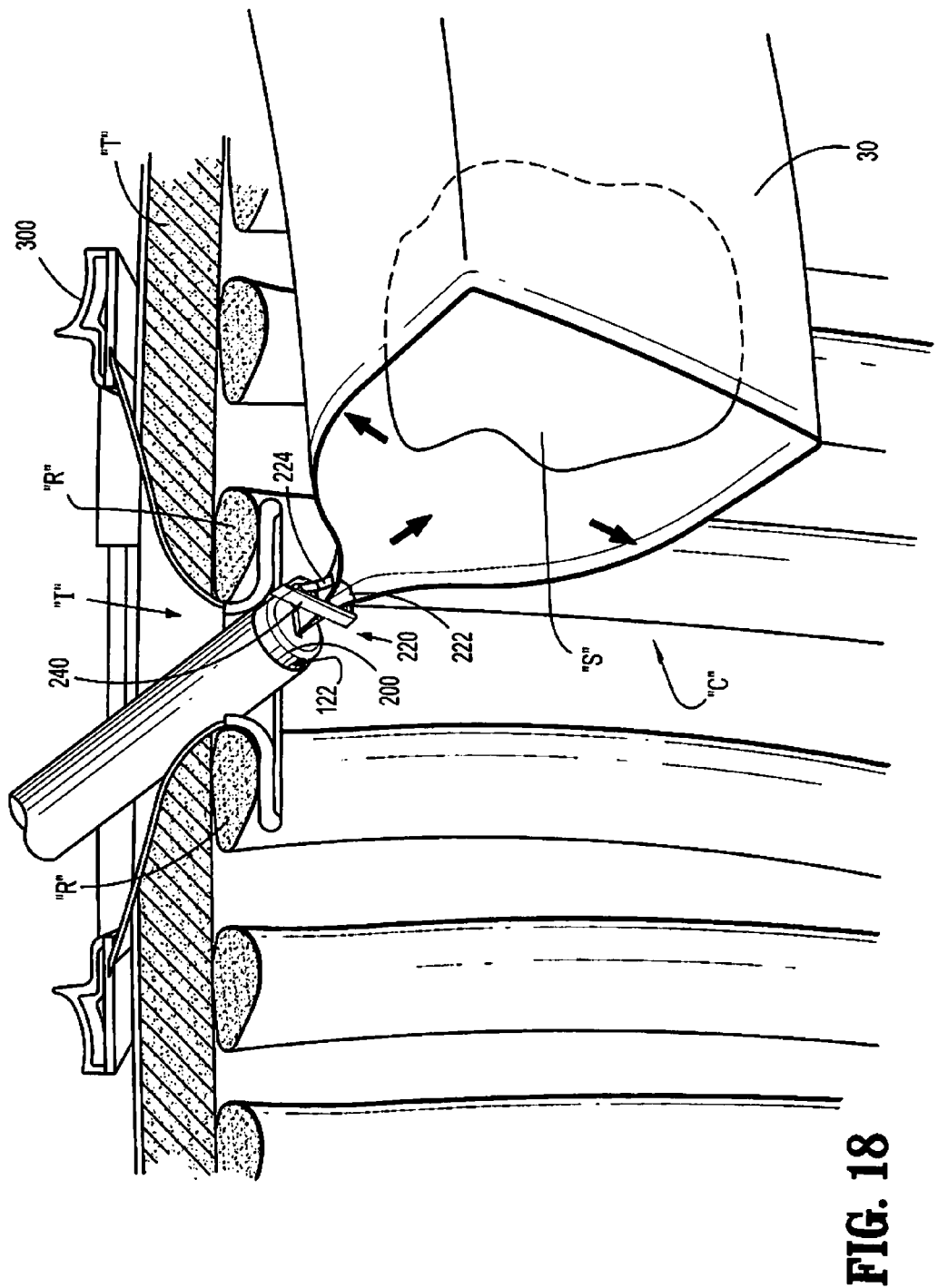
FIG. 18 is a transverse, cross-sectional view showing the surgical retrieval apparatus of FIG. 1 disposed within an internal surgical site in the deployed position with a tissue specimen disposed within the specimen retrieval bag.
Figure 19:
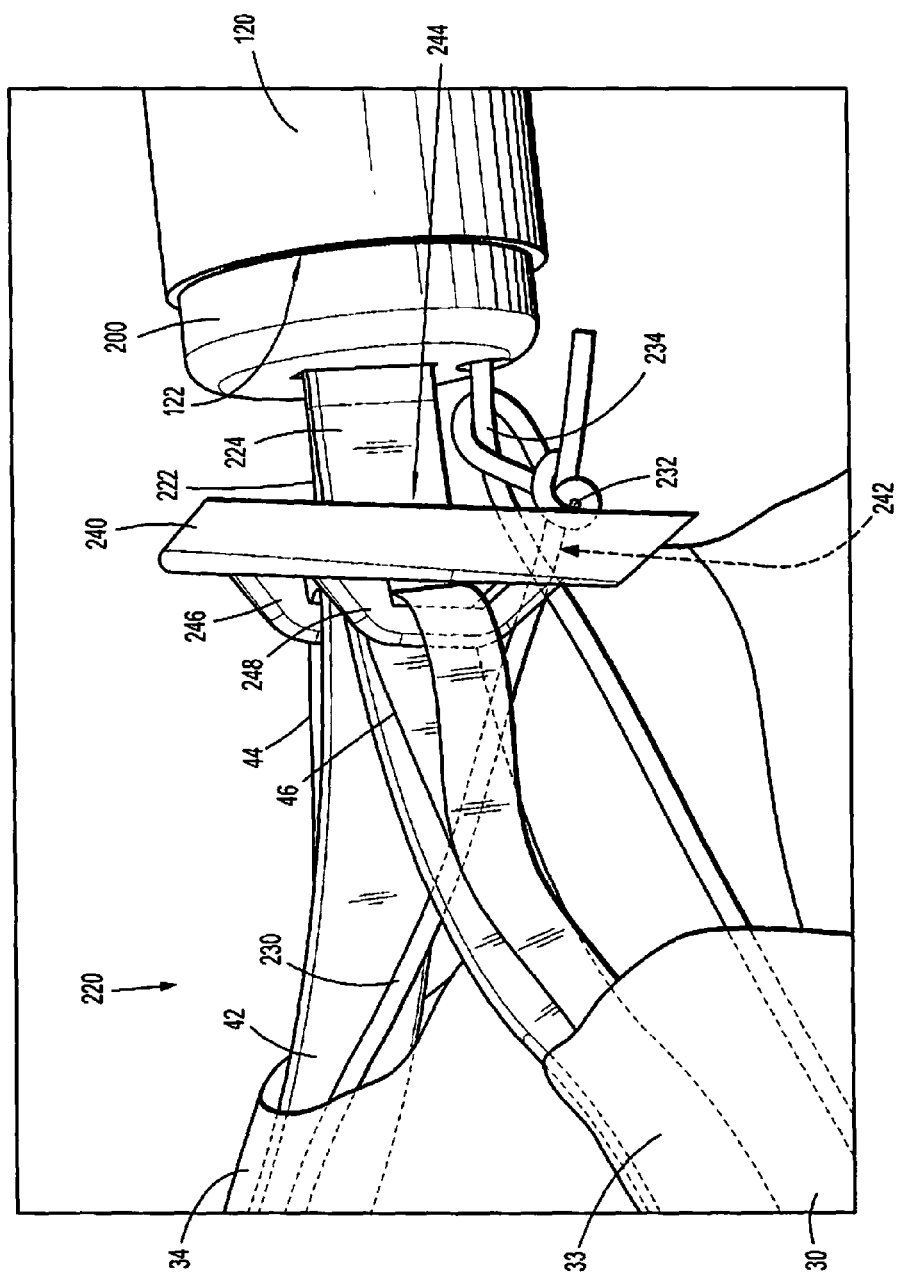
FIG. 19 is an enlarged, side view showing the stop member of FIG. 6 in use in conjunction with the surgical retrieval apparatus of FIG. 1.

With reference now to FIGS. 17-19, once surgical retrieval apparatus 10 has been inserted into the internal surgical site "C," e.g., the thoracic cavity, shaft 200 may be translated distally through channel 130, e.g., via grasping handle portion 112 of housing 100 and plunger 260 and translating plunger 260 distally relative to handle portion 112, from the retracted position to the deployed position such that end effector assembly 220 is extended from elongated sleeve 120, to deploy arms 222, 224, and specimen retrieval bag 30. More specifically, shaft 200 is translated distally through channel 130 until end effector assembly 220 and stop member 240 extend distally from elongated sleeve 120. In this position, as best shown in FIG. 17, plunger 260 is substantially mating, or flush with proximal end 102, i.e., within proximal aperture 108, of housing 100 such that, as mentioned above, plunger 260 is inhibited from being caught on the clinician's clothing, other surgical instrumentation, etc., or from being inadvertently withdrawn from housing 100.

As can be appreciated, as end effector assembly 220 emerges from elongated sleeve 120, specimen retrieval bag 30 is deployed, or unrolled, to the open condition, as shown in FIG. 18. More specifically, the bias of support member 40 disposed within the channel of specimen retrieval bag 30 and the biasing of arms 222, 224 of end effector assembly 220 towards the spaced-apart, curvate configuration automatically transition specimen retrieval bag 30 to the open condition, wherein specimen retrieval bag 30 depends from arms 222, 224 of end effector assembly 220, upon deployment from elongated sleeve 120.

As shown in FIG. 19, upon distal advancement of shaft 200 through elongated sleeve 120 to deploy end effector assembly 220 from elongated sleeve 120, stop member 240 is likewise extended from elongated sleeve 120. Once deployed, or extended from elongated sleeve 120, stop member 240 is oriented more-perpendicularly relative to elongated sleeve 120 such that stop member 240 is inhibited from returning proximally into lumen 122 of elongated sleeve 120. In other words, stop member 240 defines a long diameter or transverse dimension that is greater than the diameter or transverse dimension of lumen 122 of elongated sleeve 120 such that stop member 240 is only permitted to pass therethrough in an obliquely-angled orientation. Thus, once oriented in the substantially-perpendicular position, stop member 240 is inhibited from translating back into lumen 122 of elongated sleeve 120. As mentioned above, looped ends 44, 46 of strap 42 are engaged to supports 246, 248 of stop member 240 such that specimen retrieval bag 30 is secured to stop member 240. Further, first and second ends 232, 234 of cinch cord 230 extend through cinch cord aperture 242 of stop member 240 in a substantially un-tensioned condition due to the maintained engagement of pull-ring 280 within plunger 260 (see FIG. 17).

With end effector assembly 220 of surgical retrieval apparatus 10 disposed within the internal surgical site "C" in the deployed condition such that specimen retrieval bag 30 is disposed in the open condition, the tissue specimen "S" is moved into specimen retrieval bag 30, e.g., via manipulation of surgical retrieval apparatus 10 and/or via use of additional surgical instrumentation (e.g., a surgical grasper (not shown) inserted through another incision). Once the tissue specimen "S" to be retrieved is disposed within specimen retrieval bag 30, specimen retrieval bag 30 may be cinched closed and removed from the internal surgical site "C."

Figure 20:
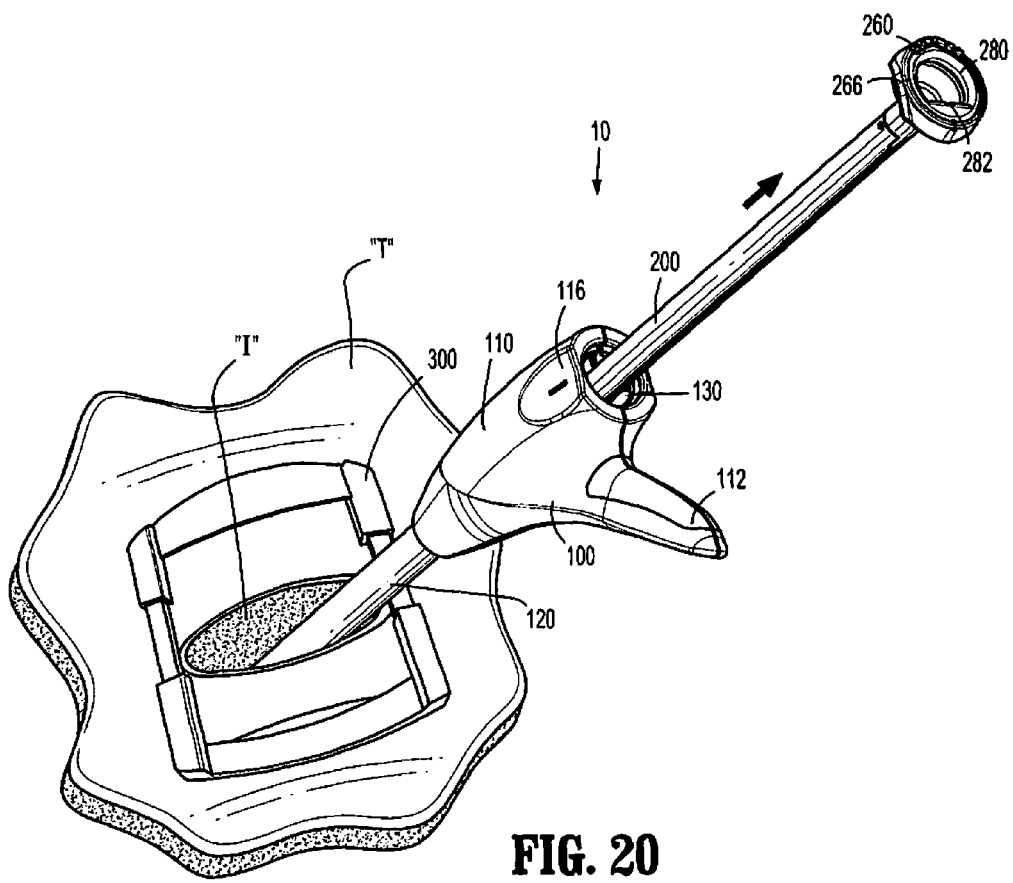
FIG. 20 is a side, perspective view of the surgical retrieval apparatus of FIG. 1, shown positioned through an incision in tissue and returning to the retracted position.
Figure 21:
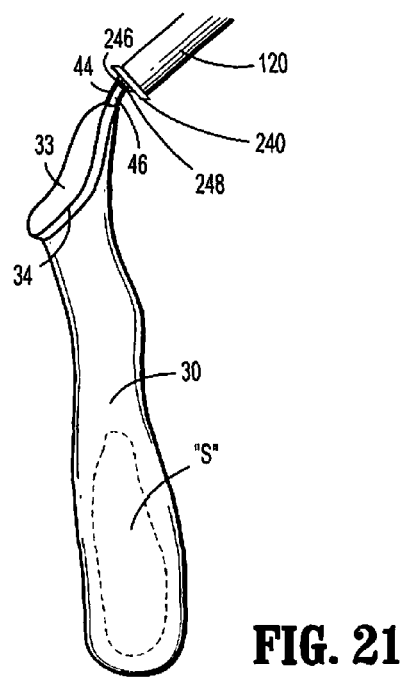
FIG. 21 is a side view of the distal end of the surgical retrieval apparatus of FIG. 1, wherein the surgical retrieval apparatus has been returned to the retracted position.

Referring now to FIGS. 20-21, in conjunction with FIGS. 1-20, in order to cinch closed specimen retrieval bag 30 to secure the tissue specimen "S" therein, plunger 260 is pulled proximally relative to housing 100 from the deployed position back to the retracted position. More specifically, the clinician grasps handle portion 112 of housing 100 with one hand, grasps flanges 266 of plunger 260 with the other hand, and translates plunger 260 and, thus, shaft 200 distally relative to housing 100. As mentioned above, detents 116 defined within housing 100 facilitate the grasping of flanges 266 to retract plunger 260.

Proximal translation of shaft 200 relative to housing 100 and elongated sleeve 120 translates arms 222, 224 of end effector assembly 220 proximally through opening of stop member 240 and into lumen 122 of elongated sleeve 120 and likewise translates cinch cord 230 proximally therethrough to at least partially cinch-closed specimen retrieval bag 30. However, due to the substantially perpendicular positioning of stop member 240 relative to elongated sleeve 120, stop member 240 is inhibited from returning through lumen 122 of elongated sleeve 120. Arms 222, 224 of end effector assembly 220 are urged toward one another by the internal wall of elongated sleeve 120 during proximal translation of shaft 200 such that arms 222, 224 pass through opening 244 defined through stop member 240 and into elongated sleeve 120, while stop member 240 abuts distal end 124 of elongated sleeve 120 such that stop member 240 and specimen retrieval bag 30, which is engaged thereto (via looped ends 44, 46 of strap 42 and supports 246, 248, respectively, of stop member 240) remain disposed distally of elongated sleeve 120. As can be appreciated, during proximal translation of arms 222, 224 of end effector assembly 220 relative to specimen retrieval bag 30, arms 222, 224 are withdrawn from loop 34 of specimen retrieval bag 30, thus disengaging specimen retrieval bag 30 therefrom.

With continued reference to FIGS. 20-21, plunger 260 and, thus, shaft 200 are returned proximally back to the retracted position, wherein shoulder 214 of shaft 200 contacts internal support 118 of housing 100 to inhibit further proximal translation of shaft 200 relative to housing 100. Shaft 200 is once again retained in this retracted position via the frictional engagement between O-rings 216 and the inner surface of housing 100. Further, as mentioned above, due to the proximal translation of shaft 200 relative to stop member 240 and specimen retrieval bag 30, specimen retrieval bag 30 is at least partially cinched closed as shaft 200 is moved to the retracted position.

Turning now to FIGS. 22-23, in order to fully cinch-closed specimen retrieval bag 30, pull-ring 280 is disengaged from plunger 260 and is translated proximally relative thereto. More specifically, the clinician inserts one or more fingers through opening 286 defined through pull-ring 280 and into recessed proximal portion 272 of plunger 260 to grasp inwardly-extending lip 282 of pull-ring 280. Translating pull-ring 280 distally with sufficient urging disengages pull-ring 280 from resilient lock tabs 274 such that pull-ring 280 may be translated proximally with respect to plunger 260 and, thus, shaft 200. As mentioned above, second end 234 of cinch cord 230 is disposed through aperture 284 of pull-ring 280 and is knotted on a proximal side thereof such that translating pull-ring 280 relative to plunger 260 translates cinch cord 230 proximally to fully cinch specimen retrieval bag 30 closed, as shown in FIGS. 22-23.

Figure 25:
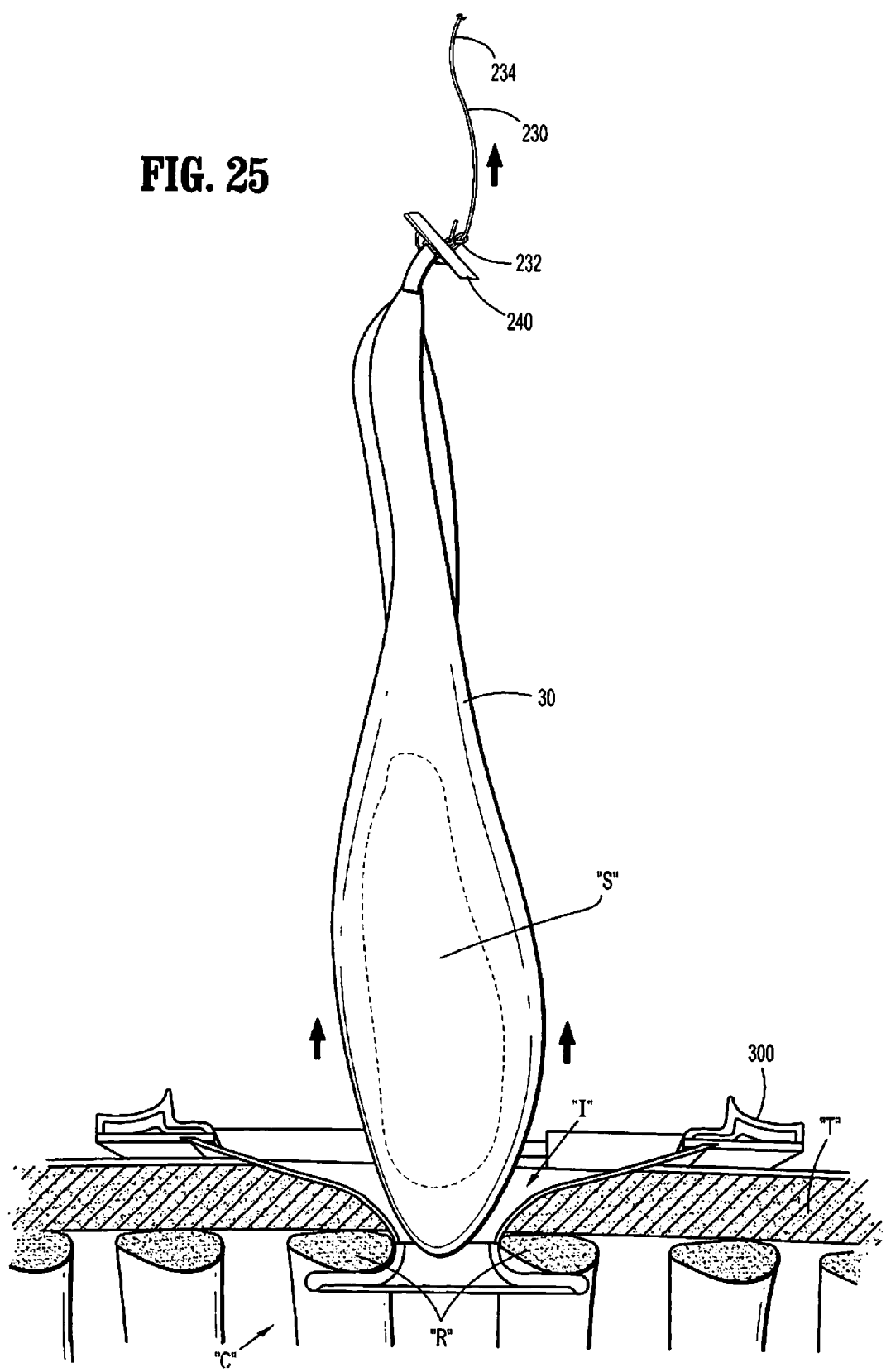
FIG. 25 is a transverse, cross-sectional view showing the specimen retrieval bag being removed through the incision in tissue with a tissue specimen disposed therein.

With reference now to FIGS. 24-25, the looping of first end 232 of cinch cord 230 about second end 234 thereof on the proximal side of stop member retains cinch cord 230 in position, i.e., the looping of cinch cord 230 inhibits un-tensioning of cinch cord 230, thereby maintaining specimen retrieval bag 30 in the cinched-closed condition. As such, cinch cord 230 may be cut to release cinch cord 230, stop member 240 and specimen retrieval bag 30 from the remainder of surgical retrieval apparatus 10, i.e., housing 100, elongated sleeve 120 and shaft 200. More specifically, cinch cord 230 is inserted into recess 270 of plunger 260 and into contact with sharpened edge 269 of blade 268 to cut cinch cord 230.

Thereafter, the other components of surgical retrieval apparatus 10, i.e., housing 100, elongated sleeve 120 and shaft 200, may be removed from the internal surgical site "C" through access portal 300, leaving behind specimen retrieval bag 30, which is disposed in the closed condition with the tissue specimen "S" therein, stop member 240, which remains secured to looped ends 44, 46 of strap 42 of specimen retrieval bag 30, and cinch cord 230, which extends from specimen retrieval bag 30 to the second, cut end 234 thereof. Ultimately, the cut end 234 of cinch cord 230 is translated proximally to remove specimen retrieval bag 30 and the tissue specimen of tissue "S" disposed therein from the internal surgical site "C."

Figure 26:
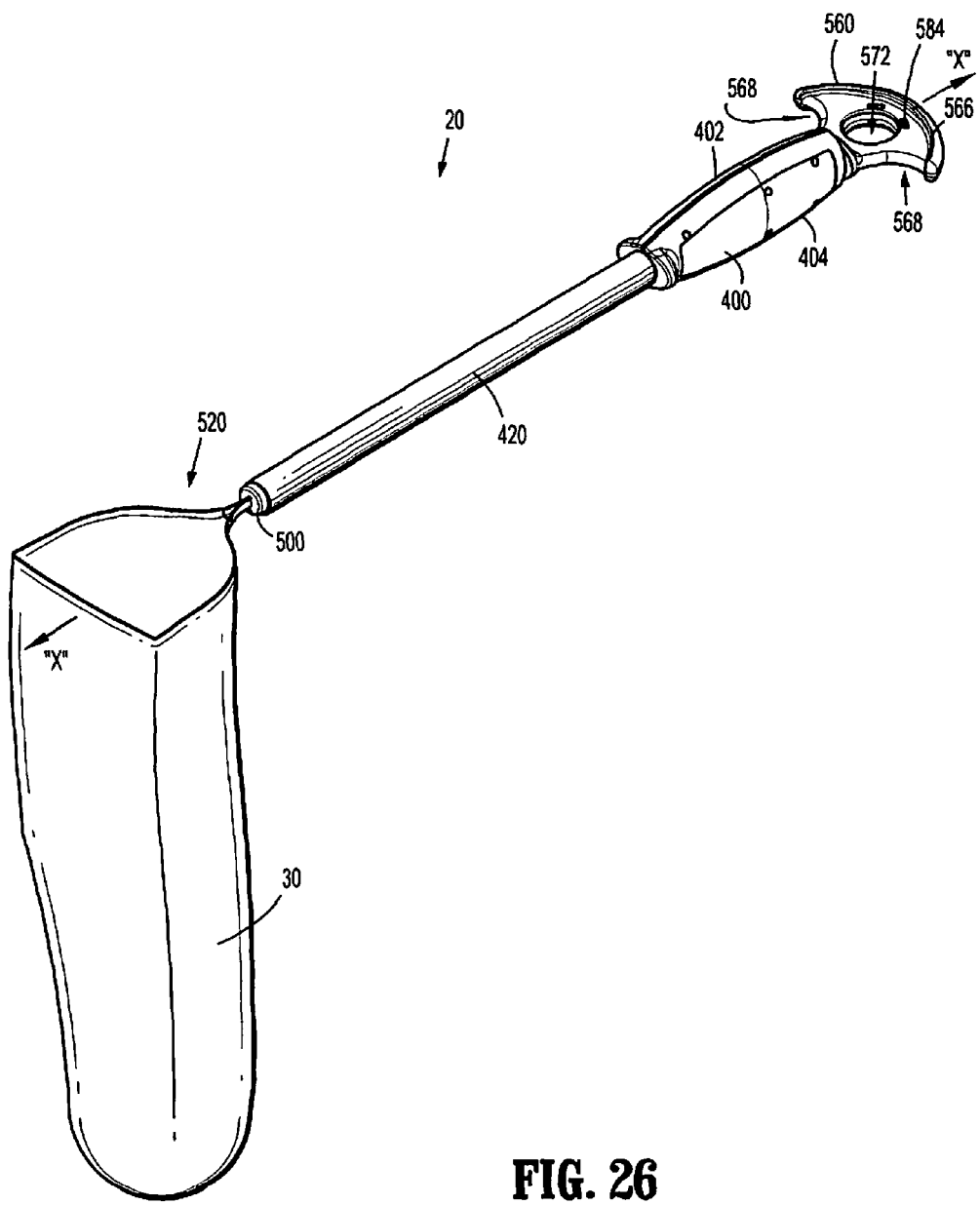
FIG. 26 is a side, perspective view of another embodiment of a surgical retrieval apparatus provided in accordance with the present disclosure.
Figure 27:
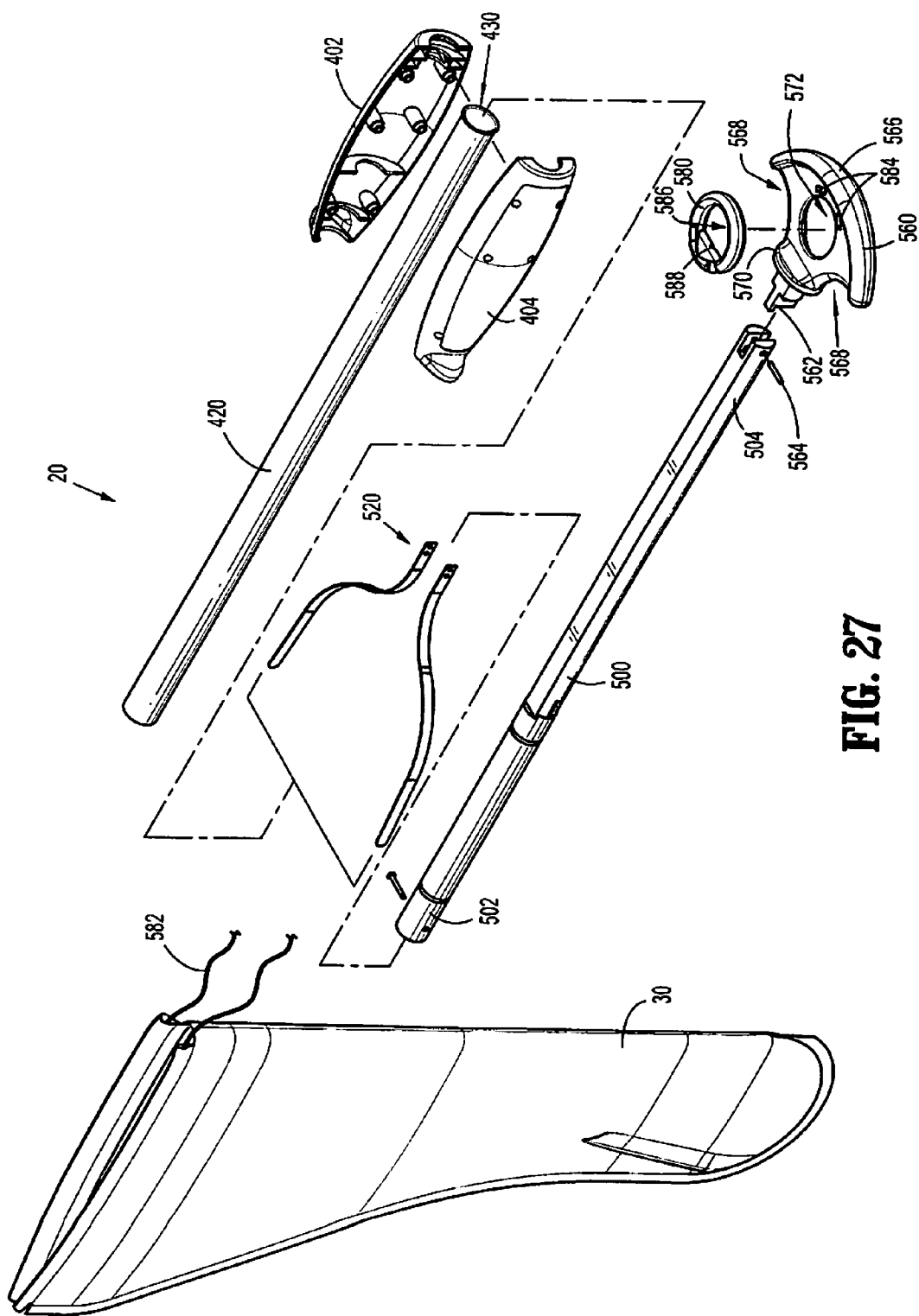
FIG. 27 is an exploded, perspective view of the surgical retrieval apparatus of FIG. 26.

Turning now to FIGS. 26-27, another embodiment of a surgical retrieval apparatus, similar to surgical retrieval apparatus 10 (FIGS. 1-25), provided in accordance with the present disclosure is shown generally identified by reference numeral 20. Surgical retrieval apparatus 20 generally includes a housing 400 having an elongated sleeve 420 fixedly engaged thereto and extending distally therefrom, and a shaft 500 having an end effector assembly 520 disposed at a distal end 502 thereof and a plunger 560 disposed at a proximal end 504 thereof. Surgical retrieval apparatus 20 is substantially similar to surgical retrieval apparatus 10 (FIGS. 1-25) in both configuration and operation and, thus, only the differences between surgical retrieval apparatus 20 and surgical retrieval apparatus 10 (FIGS. 1-25) will be described in detail hereinbelow to avoid unnecessary repetition.

Housing 400 of surgical retrieval apparatus 20 is formed from a pair of cooperating housing components 402, 404, e.g., via snap-fitting, and defines a generally-cylindrical configuration disposed about longitudinal axis "X-X." Elongated sleeve 420 extends distally from housing 400 similarly along longitudinal axis "X-X." Housing 400 and elongated sleeve 420 cooperate with one another to define a channel 430 disposed about longitudinal axis "X-X" and extending completely through surgical retrieval apparatus 20. Shaft 500 is longitudinally translatable through channel 430 between a retracted position and a deployed position to deploy end effector assembly 520 and specimen retrieval bag 30.

Shaft 500 includes a plunger 560 disposed at proximal end 504 thereof. More specifically, shaft 500 includes a bifurcated proximal end 504 and plunger 560 includes a distal protrusion 562 extending therefrom that is configured to be received within the bifurcated proximal end 504 of shaft 500. A pin 564 inserted through each of the bifurcated portions of proximal end 504 of shaft 500 and through protrusion 562 of plunger 560 secures plunger 560 to proximal end 504 of shaft 500.

Plunger 560 defines a semi-circular configuration wherein the rounded end 566 thereof faces generally proximally. Plunger 560 further includes a pair of opposed semi-circular recesses 568, defined within a distal surface 570 thereof for receipt of the clinician's fingers to facilitate translation of plunger 560 and, thus, shaft 500 between the retracted and deployed positions. Plunger 560 also includes a central aperture 572 extending therethrough in a direction generally transverse to longitudinal axis "X-X" that may additionally, or alternatively, be used to facilitate translation of shaft 500 between the retracted and deployed positions.

A pull-ring 580 including one end of cinch cord 582 secured thereto thereto is releasably couplable to plunger 560 to close specimen retrieval bag 30. More specifically, one or more resilient lock tabs 584 are positioned on plunger 560 adjacent central aperture 572 for releasably securing pull-ring 580 thereon. Further, pull-ring 580 includes a central opening 586 that is configured to substantially align with central aperture 572 of plunger 560 when engaged thereto. A lip 588 extending inwardly into central opening 586 of pull-ring 580 facilitates grasping of pull-ring 580 for releasing pull-ring 580 from plunger 560, e.g., to cinch closed specimen retrieval bag 30, similarly as described above with reference to surgical retrieval apparatus 10 of FIGS. 1-25.

The use, operation, and additional features of surgical retrieval apparatus 10 discussed above with respect to FIGS. 1-25 apply similarly to surgical retrieval apparatus 20 and, thus, will not be repeated here.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical retrieval apparatus, comprising:
   a housing defining a longitudinal axis and including an elongated sleeve extending distally therefrom, the housing and the elongated sleeve cooperating to define a lumen extending longitudinally therethrough;
   a shaft having an end effector assembly disposed at a distal end thereof, the shaft selectively translatable between a first position, wherein the end effector assembly is disposed within the elongated sleeve, and a second position, wherein the end effector assembly extends distally from the elongated sleeve;
   a specimen retrieval bag releasably coupled to the end effector assembly, the specimen retrieval bag deployable from an undeployed position to an extended position upon movement of the end effector assembly from the first position to the second position;
   a stop member disposed about the end effector assembly between the specimen retrieval bag and the shaft, the stop member configured to inhibit the specimen retrieval bag from returning within the lumen upon translation of the shaft from the second position back to the first position, the stop member defining a cinch cord aperture extending therethrough; and
   a cinch cord defining a first end, and second end, and a loop portion between the first and second ends, the loop portion positioned distally of the stop member and disposed about an open end of the specimen retrieval bag, the first and second ends extending proximally through the cinch cord aperture of the stop member, the first end knotted proximally adjacent the stop member to inhibit distal translation of the first end through the cinch cord aperture, the second end extending proximally through the shaft.

2. The surgical retrieval apparatus according to claim 1, further comprising a plunger disposed at a proximal end of the shaft and a pull-member releasably coupled to the plunger, the pull-member having the second end of the cinch cord coupled thereto, the pull-member configured, upon release from the plunger, for selective proximal translation relative to the plunger to cinch closed the specimen retrieval bag.

3. The surgical retrieval apparatus according to claim 1, further comprising a channel extending within the specimen retrieval bag and extending along at least a portion of the length of the specimen retrieval bag wherein the channel is configured to evacuate air from the specimen retrieval bag.

4. The surgical apparatus of claim 3, wherein the channel includes an open cell foam material positioned therein.

5. The surgical retrieval apparatus according to claim 1, further comprising a safety tab configured to engage both the housing and the shaft when the shaft is disposed in the first position to inhibit relative movement between the housing and the shaft.

6. The surgical retrieval apparatus according to claim 1, wherein the housing includes a pistol grip.

7. The surgical retrieval apparatus according to claim 1, wherein the specimen retrieval bag includes a strap coupled thereto that is secured to the stop member and the stop member includes a distally extending support to receive an end of the strap.

8. The surgical retrieval apparatus according to claim 1, further comprising a plunger positioned proximally of the shaft, wherein the plunger is configured to mate with the housing when the shaft is disposed in the second position.

9. The surgical retrieval apparatus according to claim 8, wherein the housing includes at least one detent and the plunger includes at least one flange, the at least one detent of the housing positioned adjacent to the at least one flange of the plunger when the shaft is disposed in the second position, the at least one detent and the at least one flange cooperable with one another to facilitate translation of the shaft from the second position back to the first position.

10. The surgical retrieval apparatus of claim 1, wherein the end effector assembly includes a pair of arms configured to receive the specimen retrieval bag thereon, the arms separable from the bag after closing the bag and withdrawal of the shaft, and the arms extend through an opening in the stop member.

11. The surgical retrieval apparatus according to claim 1, further comprising a plunger positioned proximally of the shaft and a pull-member releasably coupled to the plunger, wherein the plunger includes at least one resilient lock tab configured to releasably engage the pull-member thereon and a blade engaged thereto, the blade configured to facilitate cutting of the cinch cord to disengage the specimen retrieval bag from the shaft.

12. The surgical retrieval apparatus according to claim 1, wherein a diameter of the shaft is larger than a diameter of the opening to prevent proximal movement of the stop member over the shaft, and such that the stop member is positioned within the sleeve in an angled position and pivots when advanced from the shaft to prevent retraction into the shaft.

13. The surgical retrieval apparatus according to claim 1, wherein the shaft includes a shoulder defined on an outer periphery thereof, the shoulder configured to inhibit translation of the shaft proximally of the first position.

14. The surgical retrieval apparatus according to claim 1, wherein translation of the shaft from the second position back to the first position at least partially cinches closed the specimen retrieval bag.

15. The surgical retrieval apparatus according to claim 1, further comprising at least one O-ring disposed about the shaft, the at least one O-ring configured to frictionally retain the shaft in position relative to the housing and the elongated sleeve.

* * * * *